(12) United States Patent
Jung et al.

(10) Patent No.: US 8,287,896 B2
(45) Date of Patent: *Oct. 16, 2012

(54) SCAFFOLDS WITH TRACE ELEMENT FOR TISSUE REGENERATION IN MAMMALS

(75) Inventors: Steven B. Jung, Rolla, MO (US); Delbert E. Day, Rolla, MO (US)

(73) Assignee: The Curators of the University of Missouri, Columbia, MO (US)

( * ) Notice: Subject to any disclaimer, the term of this patent is extended or adjusted under 35 U.S.C. 154(b) by 23 days.

This patent is subject to a terminal disclaimer.

(21) Appl. No.: 12/683,280

(22) Filed: Jan. 6, 2010

(65) Prior Publication Data

US 2011/0165217 A1 Jul. 7, 2011

(51) Int. Cl.
*A61F 2/02* (2006.01)
*A61F 2/00* (2006.01)

(52) U.S. Cl. .................................................. 424/423

(58) Field of Classification Search .................. 424/423, 424/445, 618, 630, 673, 646, 639, 722; 602/43
See application file for complete search history.

(56) References Cited

U.S. PATENT DOCUMENTS

| | | | |
|---|---|---|---|
| 4,131,597 A | 10/1889 | Burleigh | |
| 4,512,038 A | 4/1985 | Alexander et al. | |
| 5,204,106 A * | 4/1993 | Schepers et al. | 424/423 |
| 5,534,244 A | 7/1996 | Tung | |
| 5,691,256 A | 11/1997 | Taguchi et al. | |
| 6,143,318 A | 11/2000 | Gilchrist et al. | |
| 6,447,805 B1 | 9/2002 | Healy | |
| 6,709,744 B1 * | 3/2004 | Day et al. | 428/403 |
| 2002/0160175 A1 | 10/2002 | Pirhonen | |
| 2004/0078077 A1 | 4/2004 | Binette et al. | |
| 2004/0170692 A1 * | 9/2004 | Day et al. | 424/489 |
| 2004/0253321 A1 | 12/2004 | Fechner et al. | |
| 2005/0021152 A1 | 1/2005 | Ogle et al. | |
| 2005/0064193 A1 | 3/2005 | Fechner et al. | |
| 2005/0102035 A1 | 5/2005 | Grundei | |
| 2005/0169967 A1 | 8/2005 | Gilchrist et al. | |
| 2005/0255159 A1 | 11/2005 | Hyers et al. | |
| 2006/0204738 A1 | 9/2006 | Dubrow et al. | |
| 2006/0233887 A1 | 10/2006 | Day | |
| 2008/0066495 A1 | 3/2008 | Moimas et al. | |
| 2008/0206714 A1 | 8/2008 | Schmitt | |

(Continued)

FOREIGN PATENT DOCUMENTS

EP 1716873 A1 11/2006

(Continued)

OTHER PUBLICATIONS

Waser et al., Chem One, McGraw Hill, Inc. (1976), 5 pages.*

(Continued)

*Primary Examiner* — Jason M Sims
*Assistant Examiner* — Miriam A Levin
(74) *Attorney, Agent, or Firm* — Senniger Powers LLP

(57) ABSTRACT

A scaffold for implantation into a mammal to facilitate vessel growth in repair, regeneration, and/or proliferation of bodily tissue, where the scaffold is based on a borate, silicate, or phosphate, glass-former and is biodegradable upon implantation in mammals. The scaffold includes one or more trace elements from the group consisting of Cu, F, Fe, Mn, Mo, Ni, Sr, and Zn which are released into the host to support vessel growth. A method involves implantation of such scaffolds.

24 Claims, 8 Drawing Sheets

U.S. PATENT DOCUMENTS

| | | |
|---|---|---|
| 2008/0249637 A1 | 10/2008 | Asgari |
| 2009/0208428 A1 | 8/2009 | Hill et al. |
| 2009/0276056 A1 | 11/2009 | Bose et al. |

FOREIGN PATENT DOCUMENTS

| | | |
|---|---|---|
| GB | 2037735 A * | 7/1980 |
| WO | 80/02378 | 11/1980 |
| WO | 9854104 | 12/1998 |
| WO | 2007124511 | 11/2007 |
| WO | 2007/144662 A1 | 12/2007 |

OTHER PUBLICATIONS

Holmes et al., Protected Bone Regeneration, Scientific Data Series in Resorbable Fixation, Medtronic Sofamor Danek (2001) [Downloaded Jun. 9, 2011] [Retrieved from internet <URL: http://www.fracture-research.de/deutsch/aktuelles/Britt%20Habil/pdfs/Protected_Bone.pdf >], 11 pages.*

Wikipedia, Aluminum Oxide [Downloaded Jun. 15, 2011] [Retrieved from internet <URL: http://en.wikipedia.org/wiki/Aluminium_oxide >], 2 pages.*

Wikipedia, Boron Trioxide [Downloaded Jun. 6, 2011] [Retrieved from internet <URL: http://en.wikipedia.org/wiki/Boron_trioxide >], 1 page.*

Wikipedia, Calcium Oxide [Downloaded Jun. 6, 2011] [Retrieved from internet <URL: http://en.wikipedia.org/wiki/CaO >], 1 page.*

Wikipedia, Copper (II) oxide [Downloaded Jun. 8, 2011] [Retrieved from internet <URL: http://en.wikipedia.org/wiki/Copper(II)_oxide >], 1 page.*

Wikipedia, Sodium Oxide [Downloaded Jun. 6, 2011] [Retrieved from internet <URL: http://en.wikipedia.org/wiki/Na2O >], 1 page.*

Wikipedia, Magnesium Oxide [Downloaded Jun. 6, 2011] [Retrieved from internet <URL: http://en.wikipedia.org/wiki/MgO >], 1 page.*

Wikipedia, Phosphorous Pentoxide [Downloaded Jun. 6, 2011] [Retrieved from internet <URL: http://en.wikipedia.org/wiki/P2O5 >], 1 page.*

Mir et al. (Adequate Serum Copper Concentration Could Improve Bone Density, Postpone Bone Loss and Protect Osteoporosis in Women, Iranian Journal of Public Health (2007), A supplementary Issue on Osteoporosis, pp. 24-29), [Downloaded Nov. 11, 2011] [Retrieved from internet <URL: http://journals.tums.ac.ir/upload_files/pdf/3678.pdf >], 6 pages.*

Holmes et al. (Protected Bone Regeneration, Scientific Data Series in Resorbable Fixation, Medtronic Sofamor Danek (2001) [Downloaded Jun. 9, 2011] [Retrieved from internet <URL: http://www.fracture-research.de/deutsch/aktuelles/Britt%20Habil/pdfs/Protected_Bone.pdf >]).*

International Preliminary Report on Patentability for PCT/US2010/041854, issued Jan. 17, 2012. (7 pages).* email cover letter from Paul Fleischut, Jul. 26, 2012 (2 pages).*

Draft claim amendments from Paul Fleischut, Jul. 26, 2012 (10 pages).*

International Preliminary Report on Patentability for PCT/US2010/041773, issued Jan. 17, 2012. (7 pages).*

Yao, Aihua et al., "In Vitro Bioactive Characteristics of Borate-Based Glasses with Controllable Degradation Behavior", Journal of the American Ceramic Society, vol. 90 Issue 1, Nov. 7, 2006, pp. 303-306.

Ning, Jia et al., "Synthesis and in Vitro Bioactivity of a Borate-Based Bioglass", Materials Letters, vol. 61, Issue 30, Dec. 2007, pp. 5223-5226.

Liang, Wen, "Bioactive Comparison of a Borate, Phosphate and Silicate Glass", Journal of Materials Research, vol. 21, Issue 1, 2005, pp. 125-131.

Jung, Steven, "Conversion Kinetics of Silicate, Borosilicate, and Borate Bioactive Glasses to Hydroxyapatite", Physics and Chemistry of Glasses—European Journal of Glass Science and Technology Part B, Apr. 2009, vol. 50, No. 2, pp. 85-88.

Liang, Wen et al., "Bioactive Borate Glass Scaffold for Bone Tissue Engineering", Journal of Non-Crystalline Solids, Journal of Non-Crystalline Solids, vol. 354, Issues 15-16, Mar. 15, 2008, pp. 1690-1696.

Liu et al., "Bioactive borosilicate glass scaffolds: improvement on the strength of glass-based scaffolds for tissue engineering", Journal of Material Science: Materials in Medicine, vol. 20, No. 1, Sep. 2008, pp. 365-372.

Rahaman et al, "Preparation and Bioactive Characteristics of Porous Borate Glass Substrates", Ceramic Engineering and Science Proceedings, vol. 26, No. 6, 2005, pp. 3-10.

Yao et al., "Preparation of Bioactive Glasses with Controllable Degradation Behavior and their Bioactive Characterization", Chinese Science Bulletin, vol. 52, No. 2, Jan. 2007, pp. 272-276.

International Search Report, PCT/US2010/041854, dated Sep. 14, 2010, 3 pages.

Written Opinion, PCT/US2010/041854, dated Sep. 14, 2010, 6 pages.

Day, R.M., Bioactive Glass Stimulates the Secretion of Angiogenic Growth Factors and Angiogenesis in Vitro, 2005, Tissue Engineering, vol. 11, No. 516, pp. 768-777.

Kokubo et al., How useful is SBF in predicting in vivo bone activity?, 2006, Biomaterials 27 (2006) 2907-2915.

Li et al, "An Investigation of Bioactive Glass Powders by Sol-Gel Processing," [online abstract], Journal of Applied Biomaterials, 1991, vol. 2, Issue 4, pp. 231-239.

"A New Generation of Bioactive Materials Useful for Bone and Tissue Repair," Missouri University of Science and Technology, Sep. 13, 2010, <http://www.ibridgenetwork.org/file_records/show/8512>.

Conzone et al., "Preparation and properties of porous microspheres made from borate glass", J Biomed Mater Res A. Feb. 2009;88(2):531-42.

International Preliminary Report on Patentability, PCT/US2010/041854, dated Jan. 17, 2012, 8 pages.

Neel et al., "Characterisation of antibacterial copper releasing degradable phosphate glass fiber", Biomaterials 26 (2005) 2247-2254).

Non-Final Office Action, U.S. Appl. No. 12/504,489, dated Apr. 19, 2012, 20 pages.

Richard, M., Bioactive Behavior of a Borate Glass, MS Thesis, UM-Rolla (2000).

* cited by examiner

SCAFFOLDS WITH TRACE ELEMENT FOR TISSUE REGENERATION IN MAMMALS

STATEMENT OF GOVERNMENT INTEREST

This invention was made with Government support under Department of the Army contract W81XWH-08-1-7065. The Government may have certain rights in the invention.

FIELD OF THE INVENTION

This invention relates to biocompatible compositions for surface and subsurface implantation into mammals to facilitate tissue repair, regeneration, and proliferation.

BACKGROUND OF THE INVENTION

Silicate-based glasses have been used as a basis for implantable compositions to support the bonding, growth or genesis of bone by fostering a supportive environment between the material and living, bone progenitor cells. It is widely recognized that successful bioactive glasses include calcium and silica in order to foster the needed supportive environment. Certain of these compositions are considered bioactive since they possess surfaces capable of fostering a calcium phosphate layer which, in turn, promotes bone bonding to the material. For example, U.S. Pat. No. 5,204,106 discloses a composition termed 45S5 glass which is composed of $Na_2O$—$CaO$—$P_2O_5$—$SiO_2$.

Day et al. U.S. Pat. No. 6,709,744 describes biocompatible materials for implantation which include borate-based glass or ceramic materials containing $Na_2O$, $CaO$, $P_2O_5$, and $B_2O_3$. A specific example is a glass containing about 22.9 wt % $Na_2O$, about 22.9 wt % $CaO$, about 5.6 wt % $P_2O_5$, and about 48.6 wt % $B_2O_3$. These materials contain a high CaO concentration to facilitate the formation of hydroxyapatite when exposed to phosphorus-containing fluids in-vivo or prior to implantation. These materials are in the form of loose particulates which are loosely packed, for example in a glass capillary tube for release into a host. Liang et al., Bioactive Borate Glass Scaffold for Bone Tissue Engineering, J. Non-Crystalline Solids 354 (2008), p. 1690-96; and Yao et al., In-Vitro Bioactive Characteristics of Borate-Based Glasses with Controllable Degradation Behavior, J. Am. Cer. Soc. 90 (2007), p. 303-306 also disclose borate-based glasses formulated with high CaO for the formation of hydroxyapatite. For example, the 0B, 1B, 2B, and 3B glasses described by Yao et al. contain 0, 17.7, 35.4, and 53 wt % borate.

There is a continuing need for biocompatible materials which promote rapid repair of mammalian tissue, and especially for enhancing vascularity.

SUMMARY OF THE INVENTION

Briefly, therefore, the invention is directed to a scaffold for implantation into a mammal to facilitate vessel growth in repair, regeneration, and/or proliferation of bodily tissue, the scaffold comprising: a scaffold body of biocompatible material in a physical form selected from the group consisting of fibers, hollow fibers, tubes, ribbons, solid spheres, hollow spheres, particles, bonded particles, and combinations thereof; wherein the biocompatible material comprises from about 40 to about 80 wt % $B_2O_3$; and wherein the biocompatible material comprises one or more trace elements selected from the group consisting of Cu, Fe, Sr, and Zn chemically dissolved in the biocompatible material in a concentration between about 0.05 and 10 wt %.

In another aspect, the invention is directed to a scaffold for implantation into a mammal to facilitate vessel growth in repair, regeneration, and/or proliferation of bodily tissue, the scaffold comprising: a scaffold body comprising biocompatible material in a physical form selected from the group consisting of fibers, hollow fibers, tubes, ribbons, solid spheres, hollow spheres, particles, bonded particles, and combinations thereof which biocompatible material comprises a glass former selected from the group consisting of $B_2O_3$, $SiO_2$, $P_2O_5$, and combinations thereof, and which is biodegradable in mammalian bodily fluids; and one or more trace elements selected from the group consisting of Cu, F, Fe, Mn, Mo, Ni, Sr, and Zn chemically dissolved in the biocompatible material in a concentration between about 0.05 and 10 wt %; wherein said glass formers are concentration balanced to impart a biodegradability such that at least about 20 wt % of the biocompatible material biodegrades within six weeks of subcutaneous implantation in a Fisher 344 rat having an age between 9 and 11 weeks and a weight between 200 and 300 grams, as determined by testing on rats with a standard deviation of 25% (relative) of the biocompatible material weight and a population size of 10.

In another aspect the invention is directed to a method for facilitating vessel growth in repair, regeneration, and/or proliferation of bodily tissue in a mammal involving implantation of these scaffolds.

Other objects and features of the invention are in part apparent and in part pointed out hereinafter.

DESCRIPTION OF PREFERRED EMBODIMENTS

Figure 1:
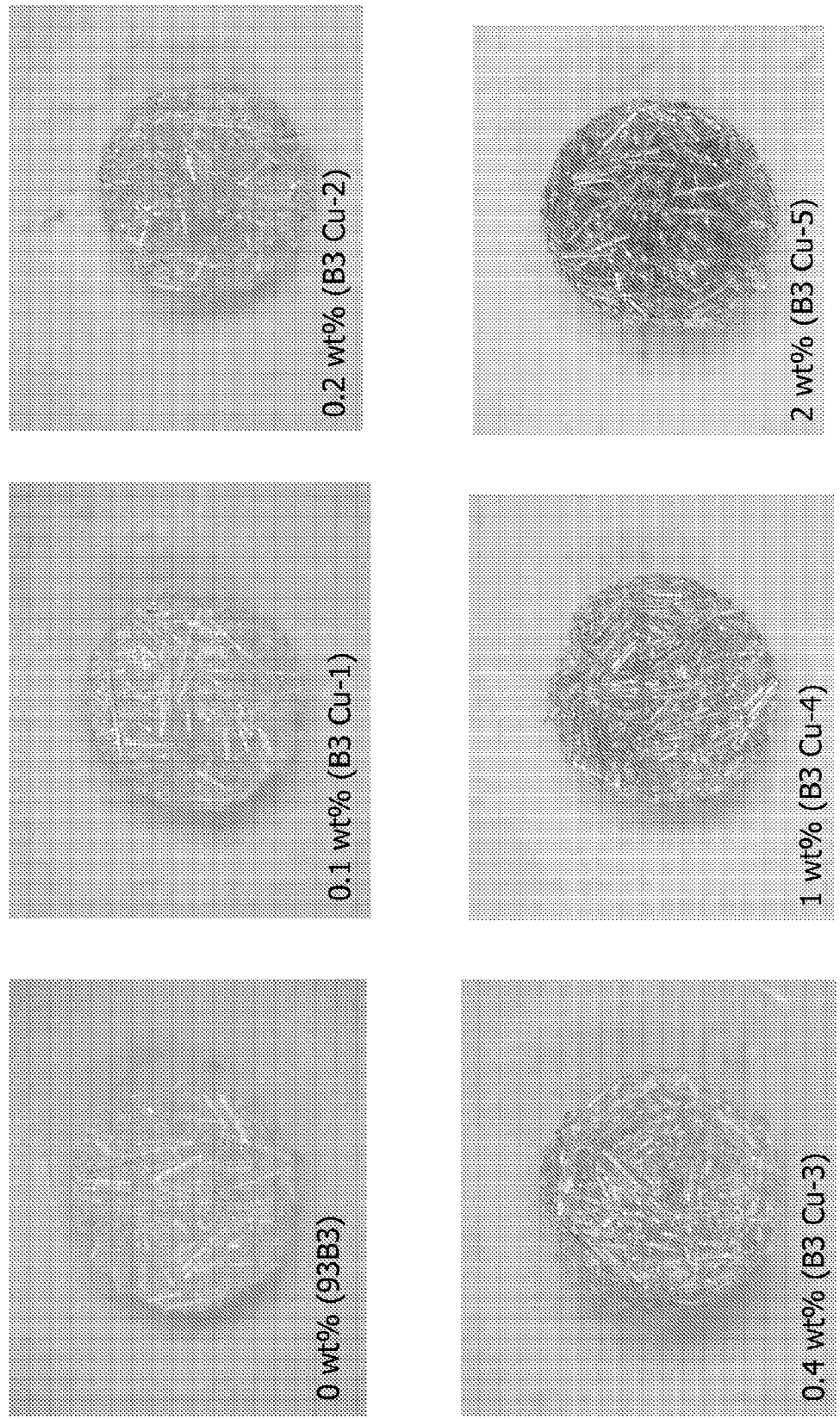
FIG. 1 is a series of photographs of scaffolds according to an Example.

In accordance with this invention, a trace element such as B, Cu, F, Fe, Mn, Mo, Si, Sr, and/or Zn is incorporated into a scaffold of a biocompatible composition which is implantable at a mammal's surface or subsurface. The scaffold composition provides ions for biological use by the mammal. These elements have beneficial effects such as an effect on endothelial cell migration which can be useful for blood vessel formation and have importance for tissue regeneration. In this way, these trace elements promote angiogenesis, which is a critical function in promoting tissue growth, such as in wound healing. This is in distinction from promoting osteoconductivity, which refers to providing bone growth factors to a site to promote bone growth. Angiogenesis, which involves increasing vascularity, i.e., vessel growth, is distinct from osteoconductivity.

The scaffold of the invention comprises a scaffold body comprising a biocompatible material in the form of one or more of fibers, hollow fibers, tubes, ribbons, solid spheres, hollow spheres, particles, bonded particles, and combinations thereof. In many of the more preferred embodiments, the form is loose or bonded fibers, or bonded particles. Generally speaking, the scaffold has a weight of at least about 10 milligrams, such as between about 10 milligrams and about 500 grams, for example between about 20 milligrams and about 2500 milligrams. The biocompatible material is borate-based, phosphate-based, and/or silicate-based and is glass, crystalline, or a combination of glass and crystalline.

The biocompatible material fibers, spheres, or other-shaped components in some embodiments are in a loose assembly of nonbonded components. Alternatively, they are bonded to each other, typically by heating, to define a scaffold body and provide a scaffold body compressive strength of greater than 0.4 MPa. The desired compressive strength is selected so that the components are in no sense free flowing, and so that the scaffold body can be handled without disintegrating into the individual body components. The desired compressive strength is also selected to provide the strength that is required to remain integral after implantation, whether for repair of a load-bearing body part or non-load-bearing part, or one subject to impact or significant movement. In some preferred embodiments, the compressive strength of the scaffold body is at least about 5 MPa, while in other embodiments where greater rigidity is required, the compressive strength is at least about 20 MPa, such as between about 20 and about 200 MPa.

The initial surface area of the scaffold varies widely depending on the scaffold morphology—for example, whether it is all fibers, the fiber dimensions, whether it is particles, the particle size, etc. Moreover, the surface area changes during biodegradation. Generally speaking, scaffolds of the fibrous morphology and generally of the dimensions in below Example 1 have a surface area/bulk scaffold volume of between about 50 and about 1000 $cm^{-1}$, such as between about 50 and about 500 $cm^{-1}$. The scaffold in Example 1 has a surface area/unit bulk volume of 134 $cm^{-1}$, based on its dimensions of being a cylinder 7 mm in diameter and 2 mm high. The surface area of the starting glass fibers was 10.27 $cm^2$ and the bulk volume of the cylinder was $7.7 \times 10^{-2}, cm^3$.

One or more selected trace elements are incorporated into the implantable material in a concentration of at least about 0.05 wt %, or at least about 0.1 wt %. In most instances, the concentration is less than 10 wt %, or less than 5 wt %, such as between about 0.05 and about 5 wt %, for example between about 0.1 and about 2.5 wt % (per element). Where the implantable biocompatible material is borate-based or phosphate-based, the trace element concentration is less than 5 wt %, and it may be higher and up to 10 wt % where the biocompatible material is silicate-based. The trace elements are selected from the group consisting of B, Cu, F, Fe, Mn, Mo, Ni, Si, Sr, and Zn. In certain preferred embodiments the trace element is one or more selected from the group consisting of Cu, F, Fe, Mn, Mo, Sr, and Zn. In some especially preferred embodiments for certain applications, the trace element is one or more selected from the group consisting of Cu, Fe, Sr, and Zn. More than one of these trace elements can be employed in a single composition. Silicon as a trace element is applicable to borate-based and phosphate-based glasses, and not to silicate-based glasses. Boron as a trace element is applicable to silicate-based and phosphate-based glasses, and not to borate-based glasses. Accordingly, the group of Cu, F, Fe, Mn, Mo, Sr, and Zn has more general applicability. Also, certain of these elements may be present in greater amounts in that they are not being used as trace elements in accordance with this invention. For example, a scaffold made of a biocompatible glass material which contains 0.4 wt % Cu and 15 wt % Sr contains Cu as a trace element in accordance with this invention; and it contains Sr, but not as a trace element in accordance with this invention. Such a material would indeed satisfy the requirement herein for a trace element from the group Cu, F, Fe, Mn, Mo, Ni, Sr, and Zn in a concentration between about 0.05 and 10 wt % by virtue of the material's Cu content, regardless of its unqualifying Sr content.

Where Cu is desired, the source of Cu to the glass or crystalline biocompatible material may be a copper oxide such as CuO or $Cu_2O$ or other copper compounds such as copper nitrate or copper sulfate, for example. In one embodiment, Cu is incorporated into the glass in a concentration of between about 0.05 and about 5 wt % (about 0.06-6 wt % CuO; about 0.055-5.5 wt % $Cu_2O$), such as between about 0.1 and about 2.5 wt % (about 0.12-3 wt % CuO; about 0.11-3 wt % $Cu_2O$). There are preferred embodiments employing from about 1 wt % to about 2 wt % Cu, as provided by between about 1.2 wt % and about 2.4 wt % CuO.

Where Sr is desired, the source of Sr to the glass or crystalline biocompatible material may be an oxide such as SrO or other Sr compounds such as $SrCO_3$, for example. In one embodiment, Sr is incorporated into the glass in a concentration of between about 0.05 and about 5 wt % (about 0.06 to 5.90 wt % SrO), such as between about 0.1 and about 2.5 wt % (about 0.12 to 2.95 wt % SrO). There are preferred embodiments employing from about 1 wt % to about 2 wt % Sr, as provided by between about 1.18 wt % and about 2.36 wt % SrO.

Where Zn is desired, the source of Zn to the glass or crystalline biocompatible material may be an oxide such as ZnO or other Zn compounds such as $Zn_3(PO_4)_2$-$xH_2O$, for example. In one embodiment, Zn is incorporated into the glass in a concentration of between about 0.05 and about 5 wt % (about 0.06 to 6.0 wt % ZnO), such as between about 0.1 and about 2.5 wt % (about 0.12 to 3.0 wt % ZnO). There are preferred embodiments employing from about 1 wt % to about 2 wt % Zn, as provided by between about 1.20 wt % and about 2.40 wt % ZnO.

Where Fe is desired, the source of Fe to the glass or crystalline biocompatible material may be an oxide such as FeO, $Fe_3O_4$, $Fe_2O_3$, or other Fe compounds such as $FeSO_4$-$7H_2O$, for example. In one embodiment, Fe is incorporated into the glass in a concentration of between about 0.05 and about 5 wt % (about 0.06 to 6.45 wt % FeO), such as between about 0.1 and about 2.5 wt % (about 0.13 to 3.23 wt % FeO). There are preferred embodiments employing from about 1 wt % to about 2 wt % Fe, as provided by between about 1.29 wt % and about 2.58 wt % FeO.

The trace element and biocompatible composition are carefully selected and formulated to provide a specifically timed release of trace element based on flow of blood or other physiological fluids through the scaffold as the biocompatible composition biodegrades in the mammalian host. The trace element is an integral component of the biocompatible composition and is chemically dissolved in the material. This is in sharp contrast to being in the form of a coating on the glass or being simply adsorbed onto the material as, for example, adsorbed onto a water insoluble implantable compound. Since the trace element is chemically dissolved in the glass material, it is released into the host mammal incrementally as the glass biodegrades, and over that same period during which the glass biodegrades. In contrast, a coating or adsorbed material is released more quickly, and its release cannot be controlled by controlling the composition of the overall glass material. In one embodiment, the trace element is generally macro-homogeneously present in the biocompatible composition to facilitate release over the entire degradation life of the composition. As blood and or other fluids flow through the scaffold and the scaffold biodegrades in the host mammal, the trace element is released to provide its advantageous angiogenic effect over time in promoting benefits to the host in the area of the implantation. So, for example, as the borate-based, phosphate-based, or silicate-based composition biodegrades, it releases trace element to promote angiogenesis.

The glass formers in certain embodiments of the invention are concentration balanced to impart the desired biodegradability. For example, in the B3-Cu1 composition of below Example 1, the concentrations of the glass formers borate, silicate, and phosphate are balanced to 52.95 wt %, 0 wt %, and 4.0 wt %, respectively, with respect to themselves and with respect to the other components in the material $Na_2O$, CaO, and $K_2O$. Balancing in this regard encompasses balancing the concentration of one glass former with other components, such as with those glasses in Table 3 which contain borate and other components, but no phosphate or silicate.

In many preferred embodiments of the scaffold, the concentrations of glass formers are balanced such that at least about 20 wt % of the biocompatible material biodegrades within six weeks of implantation in its mammalian host. For example, the concentrations of glass formers are balanced such that at least about 20 wt % of the biocompatible material biodegrades within six weeks of implantation in a Fisher 344 rat having an age between 9 and 11 weeks and a weight between 200 and 300 grams. In accord with this measure, the testing is performed on rats with a standard deviation of 25% (relative) of the biocompatible material and a population size of 10. In other words, when 10 of these scaffolds are implanted into the subcutaneous sites of rats, on average at least 20 wt % of the scaffolds' material biodegrades within six weeks; and in at least 68% of rats at least 15 wt % of the scaffold biodegrades; and in at least 90% of rats at least 10 wt % of the scaffold degrades. Implantation for this and the following standards is according to the protocol described below in Example 1. Biodegrading in most instances manifests itself either as scaffold weight loss, but can also manifest itself as another reaction of the scaffold material involving a change of composition which results in release of trace element into the host.

Similarly, in another aspect, the concentrations of glass formers are balanced such that at least about 20 wt % of the trace element concentration in the scaffold is released from the scaffold into the host within six weeks of implantation in its mammalian host. For example, the concentrations of glass formers are balanced such that at least about 20 wt % of the trace element concentration in the scaffold is released from the scaffold into the host within six weeks of implantation in a Fisher 344 rat having an age between 9 and 11 weeks and a weight between 200 and 300 grams. In accord with this measure, the testing is performed on rats with a standard deviation of 25% (relative) of the biocompatible material and a population size of 10. In other words, when 10 of these scaffolds are implanted into the subcutaneous sites of rats, on average at least 20 wt % of the scaffolds' trace element concentration is released within six weeks; and in at least 68% of rats at least 15 wt % of the scaffolds' trace element concentration is released; and in at least 90% of rats at least 10 wt % of the scaffolds' trace element concentration is released.

On the other hand, the scaffold does not biodegrade so quickly in the host that it fails to provide trace elements over a long enough period to adequately promote angiogenesis. For example, at least 50 wt % of the scaffold material remains for at least two weeks and does not biodegrade within two weeks. That is, the concentrations of glass formers are balanced such that at least about 50 wt % of the biocompatible material remains for at least two weeks after implantation in a Fisher 344 rat having an age between 9 and 11 weeks and a weight between 200 and 300 grams. In accord with this measure, the testing is performed on rats with a standard deviation of 25% (relative) of the biocompatible material and a population size of 10. In other words, when 10 of these scaffolds are implanted into the rats, on average at least 50 wt % of the scaffolds' material does not biodegrade within two weeks; and in at least 68% of rats at least 37.5 wt % of the scaffold does not biodegrade within two weeks; and in at least 90% of rats at least 25 wt % of the scaffold does not biodegrade within two weeks.

Moreover, in these embodiments, at least 50 wt % of the scaffold trace element concentration remains for at least two weeks. That is, the concentrations of glass formers are balanced such that at least about 50 wt % of the trace element remains for at least two weeks after implantation in a Fisher 344 rat having an age between 9 and 11 weeks and a weight between 200 and 300 grams. In accord with this measure, the testing is performed on rats with a standard deviation of 25% (relative) of the biocompatible material and a population size of 10. In other words, when 10 of these scaffolds are implanted into the rats, on average at least 50 wt % of the scaffolds' trace element concentration remains for at least two weeks; and in at least 68% of rats at least 37.5 wt % of the scaffolds' trace element concentration remains for at least two weeks; and in at least 90% of rats at least 25 wt % of the scaffolds' trace element concentration remains for at least two weeks.

In one embodiment of the invention the biocompatible composition releases the trace element at particular rate of release of trace element, per gram of glass, per day in a mammalian host. The release rate can in effect be "dialed in" by determining the desired amount of trace element to be released within the host, and then selecting a biocompatible composition or combination of compositions to achieve this rate. As noted above, the glass formers are concentration balanced to impart the desired biodegradability. In a related aspect, the surface area per unit volume can be controlled to control release rate, as greater surface area increases reactivity and therefore release rate. One skilled in the art appreciates that the rate of biodegradation of the glass material is different from host to host, from glass to glass, from trace element to trace element, and otherwise depends on a number of factors. For example, a more physically active host with a faster average heart rate may encourage biodegradation and therefore trace element release at a faster rate. In one embodiment, the composition has a trace element release (Cu) rate of between about 0.5 and about 100 E-7 moles of trace element, per gram of glass, per day; for example, between about 1 and about 25 E-7 moles of trace element, per gram of glass, per day; such as between about 1 and about 20 E-7 moles of trace element, per gram of glass, per day, or between about 3 and about 12 E-7 moles of trace element, per gram of glass, per day.

As an alternative perspective on trace element release for this invention, in one embodiment for certain applications, the rate of release is between about 0.1 and about 60 micromolar; i.e., between about 0.1 and about 60 micromoles trace element are released per liter of flow through the composition. In other embodiments, the composition is formulated to provide a release rate of between about 0.5 and about 30 micromolar, such as between about 3 and about 12 micromolar. For example, in one embodiment where the trace element is Cu and the composition is a borate-based or silicate-based scaffold, the scaffold composition is prepared to yield a Cu release rate during blood flow therethrough of between about 0.1 and about 60 micromolar, such as between about 0.5 and 30 micromolar, or between about 3 and about 12 micromolar.

As noted above, the biocompatible materials of the inventive scaffolds biodegrade in physiological fluids. However, in comparison to articles characterized as "water soluble" which dissolve relatively rapidly (over a period of, e.g., three weeks or less) in aqueous solutions, the biocompatible materials of the invention are not water soluble, that is, they are resistant to rapid water solubility. For example, scaffolds made from them having a surface area and size of practical application for use as an implantable scaffold do not completely dissolve in a less than several weeks (e.g., six weeks) at 37° C. in an aqueous phosphate solution or an aqueous solution with a miscible solvent such as methanol, ethanol, isopropanol, acetone, ethers or the like. As understood in the art, materials which are "water soluble" are subject to relatively rapid solubility; and materials which are "water insoluble" are either entirely insoluble in water, or are at least only dissolvable with difficulty. Generally speaking the scaffolds materials are not water insoluble and are not water soluble under this characterization; rather, they are of intermediate water solubility.

The material is biocompatible in that it is not toxic or otherwise harmful to its host's living tissue. Some of the %; and the one or more of MgO, SrO, BaO, and CaO is present in a cumulative concentration between about 1 and about 50 wt %, such as between about 5 and about 40 wt %. Where Cu is the trace element, this composition further contains 0.05 to 5; or 0.01 to 2.5 wt % Cu; as CuO, $Cu_2O$, or other Cu compound. The transition metal elements are those elements where the d-band contains less than its maximum number of ten electrons per atom, and includes, among others, Co and Ni. In fact, certain of the trace elements used in accordance with this invention such as Zn and Fe are transition metals. So in formulations where the trace element concentration of these trace elements is stated to be in a particular range such as between about 0.1 and about 2.5 wt %, of course the trace element concentration is in that range regardless of the fact that transition elements may be among the trace elements, and if Zn and Fe are present in an amount greater than 2.5 wt %, they are not trace elements.

A few exemplary glass materials of the invention are as follows:

TABLE 1

Trace-Element-Containing Borate Biocompatible Glasses (wt %)

| Glass | $B_2O_3$ | $Na_2O$ | CaO | $K_2O$ | MgO | $P_2O_5$ | CuO | SrO | ZnO | $Fe_2O_3$ |
|---|---|---|---|---|---|---|---|---|---|---|
| 1 | 52.95 | 5.99 | 19.98 | 11.99 | 5.00 | 4.00 | 0.10 | | | |
| 2 | 52.89 | 5.99 | 19.96 | 11.98 | 4.99 | 3.99 | 0.20 | | | |
| 3 | 52.79 | 5.98 | 19.92 | 11.95 | 4.98 | 3.98 | 0.40 | | | |
| 4 | 52.47 | 5.94 | 19.80 | 11.88 | 4.95 | 3.96 | 1.00 | | | |
| 5 | 51.94 | 5.88 | 19.60 | 11.76 | 4.90 | 3.92 | 2.00 | | | |
| 6 | 51.73 | 5.86 | 19.52 | 11.71 | 4.88 | 3.90 | 0.40 | 2.00 | | |
| 7 | 51.20 | 5.80 | 19.32 | 11.59 | 4.83 | 3.86 | 0.40 | 2.00 | 1.00 | |
| 8 | 50.88 | 5.76 | 19.20 | 11.52 | 4.80 | 3.84 | 0.40 | 2.00 | 1.00 | 0.40 | preferred compositions (Ca-free) of the invention are also not bioactive, in the sense that hydroxyapatite does not form. That is, they lack bioactivity, where bioactivity refers to a material's capacity in phosphorus-containing mammalian fluids to foster growth of a calcium phosphate layer or convert to bone-precursor calcium phosphate compounds which, in turn, promotes bone bonding to the material.

In one embodiment the biocompatible material into which the trace element is incorporated is a borate-based glass material containing the following, approximately, with all percentages herein being by weight, unless stated otherwise:

| | |
|---|---|
| $B_2O_3$ | 40 to 80 |
| $Na_2O$ | 0 to 25 |
| $Li_2O$ | 0 to 25 |
| $K_2O$ | 0 to 25 |
| $Rb_2O$ | 0 to 25 |
| CaO | 0 to 40 |
| MgO | 0 to 25 |
| SrO | 0 to 40 |
| BaO | 0 to 50 |
| $Li_2O + Na_2O + K_2O + Rb_2O$ | 0 to 50 cumulative |
| MgO + SrO + BaO + CaO | 0 to 50 cumulative |
| $P_2O_5$ | 0 to 10 |
| $SiO_2$ | 0 to 18 |
| $Al_2O_3$ | 0 to 3 |
| F | 0 to 4 |
| transition metal elements | 0 to 10 cumulative. |

The concentrations of $K_2O$ and MgO in certain of these embodiments are each from about 1 to about 25 wt %. In most embodiments, the one or more of $Li_2O$, $Na_2O$, $K_2O$, and $Rb_2O$ is present in a cumulative concentration between about 1 and about 50 wt %, such as between about 5 and about 20 wt In most embodiments the biocompatible material consists only or essentially of components meeting these compositional requirements or other narrower descriptions herein. But generally speaking, for some embodiments other materials not meeting these descriptions may be incorporated into the scaffolds.

Additional borate-based materials within this description, into which Cu or other stated trace element may be incorporated according to this invention, contain, by weight %, the following, keeping in mind that one or more of the other trace elements may be included in addition to Cu in analogous concentrations, or instead of Cu:

TABLE 2

Wt. % Composition of Additional Borate Glasses

| | $B_2O_3$ | $Na_2O$ | $K_2O$ | $Li_2O$ | CaO | BaO | MgO | $P_2O_5$ | CuO |
|---|---|---|---|---|---|---|---|---|---|
| A | 52.5 | 6.0 | 12.0 | | 20.0 | | 5.0 | 4.0 | 0.5 |
| B | 70.3 | | | 10.3 | 19.3 | | | | 0.1 |
| C | 63.7 | 19.0 | | | 17.2 | | | | 0.1 |
| D | 49.0 | 14.6 | | | | 36.0 | | | 0.4 |
| E | 78.4 | | | 11.5 | 10.0 | | | | 0.1 |
| F | 69.9 | | 10.0 | | 10.0 | 10.0 | | | 0.1 |
| G | 78.6 | | 11.3 | | | | 10.0 | | 0.1 |
| H | 78.6 | | 11.3 | | 10.0 | | | | 0.1 |
| I | 75.9 | | 11.0 | | 13.0 | | | | 0.1 |
| J | 58.6 | | 8.0 | | 33.0 | | | | 0.4 |

It can therefore be appreciated that in addition to the Cu, and/or in addition to Sr, Zn, Fe, Mn, F, Si, Ni, and/or Mo, the borate-based biocompatible materials include 40 to 80 wt % $B_2O_3$ or 50 to 80 wt % $B_2O_3$, or even the narrower $B_2O_3$ ranges described herein, in combination with 1 to 25 wt % $Na_2O$, 1 to 25% $K_2O$, 1 to 40 wt % CaO, 1 to 25 wt % MgO, and 1 to 10 wt % $P_2O_5$. Or the component materials may contain 40 to 80 wt % $B_2O_3$, 1 to 25 wt % $Li_2O$, and 1 to 40 wt % CaO. Or they may contain 40 to 80 wt % $B_2O_3$, 1 to 25 wt % $Na_2O$, and 1 to 40 wt % CaO. Or they may contain 40 to 80 wt % $B_2O_3$, 1 to 25 wt % $Na_2O$, and 1 to 40 wt % BaO. Or they may contain 40 to 80 wt % $B_2O_3$, 1 to 25 wt % $Li_2O$, and 1 to 25 wt % MgO. Or they may contain 40 to 80 wt % $B_2O_3$, 1 to 25 wt % $Li_2O$, and 1 to 40 wt % BaO. While the biocompatible materials hereinabove and hereinbelow are described as containing various oxides by weight %, those skilled in the art understand that in the final glass or glass/crystalline composition, the oxide compounds are dissociated, and the specific oxides, e.g., $B_2O_3$, $SiO_2$, $P_2O_5$, etc. are not separately identifiable or even necessarily separately present. Nonetheless, it is conventional in the art to refer to the final composition as containing a given % of the individual oxides, so that is done here. So from this perspective, the compositions herein are on an equivalent basis.

The biocompatible materials of the invention containing the trace element in certain preferred versions are borate-based in that they contain between about 40 and about 80 wt % $B_2O_3$, such as between about 50 and about 80 wt % $B_2O_3$. Borate-based materials have several important advantages for biological use such as their ease of preparation, ability to be made into glass particulates, microspheres or fibers at relatively low temperatures without crystallization, and, particularly, their biocompatibility. The borate-based materials disclosed herein, compared to silicate-based materials, have significantly faster reaction rates, lower melting temperatures, resistance to crystallization, and in certain instances the absence of silica, which only slowly degrades in the body. So while certain embodiments employ up to about 18 wt % $SiO_2$ in many other preferred embodiments herein, the materials are silicate-free, containing less than 0.1 wt % silicate or even no silicate. Borate glasses form hollow fibers upon reaction in-vivo, while silicate glasses do not; and they facilitate angiogenesis in-vivo. The borate materials described herein also release boron in-vivo as they react with the body fluids.

There is one embodiment which has specific preference in certain applications and wherein the concentration of Ca (elemental or in CaO or other compounds) in the material is controlled to less than about 5 wt %. Certain preferred embodiments strictly control the Ca concentration to less than about 0.5 wt %, such as to less than 0.2 wt %, and even to less than 0.1 wt %. The advantage in this embodiment to strictly controlling Ca concentration is the avoidance of the formation of calcium phosphate compounds, apatite type compounds and related amorphous calcium phosphate (ACP) upon exposure to physiological phosphorus-containing fluids. Such apatite compounds include hydroxyapatite $Ca_5(PO_4)_3(OH)$, fluoroapatite $Ca_5(PO_4)_3F$, amorphous calcium phosphate (ACP), and other calcium-containing compounds. Thus, in certain applications it is advantageous to avoid the formation of Ca-apatite compounds because they have a relatively lower radiopacity than do, for example, analogous Sr or Ba compounds. In certain situations it is advantageous to avoid Ca-apatite compounds in order to form compounds which degrade more rapidly, or perhaps even more slowly. It can also be advantageous to avoid Ca for purposes of controlling melt characteristics, such as viscosity, melting temperature, and/or crystallization tendency. The Ca-free compositions lack bioactivity, where bioactivity refers to a material's capacity in phosphorus-containing mammalian fluids to foster growth of a calcium phosphate layer or convert to bone-precursor calcium phosphate compounds.

The biocompatible Ca-free material in one embodiment into which the Cu and/or other trace element is incorporated in the concentrations described above preferably contains between about 40 and about 80 wt % $B_2O_3$ with the remainder being selected from alkali oxides and alkaline earth oxides, and other optional constituents listed below. For example, this material contains, by weight %:

| | |
|---|---|
| $B_2O_3$ | 40 to 80 |
| $Na_2O$ | 0 to 25 |
| $Li_2O$ | 0 to 25 |
| $K_2O$ | 0 to 25 |
| $Rb_2O$ | 0 to 25 |
| MgO | 0 to 25 |
| SrO | 0 to 40 |
| BaO | 0 to 25 |
| $Li_2O + Na_2O + K_2O + Rb_2O$ | 0 to 50 cumulative |
| $MgO + SrO + BaO$ | 0 to 50 cumulative |
| $P_2O_5$ | 0 to 10 |
| $SiO_2$ | 0 to 18 |
| $Al_2O_3$ | 0 to 3 |
| F | 0 to 4 |
| transition metal elements | 0 to 10 cumulative. |

In addition, the material contains Cu in a concentration of 0.05 to 5; or 0.01 to 2.5 wt %, as CuO, $Cu_2O$, or other Cu compound, and/or other trace element. Certain of these embodiments contain low levels of Ca, as described above; while others are substantially Ca-free and contain essentially no or less than 0.1 wt % Ca.

In one preferred embodiment, the material contains between about 50 and about 80 wt % $B_2O_3$; between about 5 and about 20 wt % alkali oxide component selected from the group consisting of $Li_2O$, $Na_2O$, $K_2O$, $Rb_2O$, and combinations thereof; and between about 5 and about 40% alkaline earth component selected from the group consisting of MgO, SrO, BaO, and combinations thereof. Lanthanides are specifically and strictly excluded from certain preferred embodiments. In some embodiments the biocompatible material consists essentially of between about 50 and about 80 wt % $B_2O_3$; between about 5 and about 20 wt % alkali oxide component selected from the group consisting of $Li_2O$, $Na_2O$, $K_2O$, $Rb_2O$, and combinations thereof; between about 5 and about 40 wt % alkaline earth component selected from the group consisting of MgO, SrO, BaO, and combinations thereof, and between about 0.05 and 5 wt % Cu, as CuO, $Cu_2O$, or other Cu compound Exemplary borate-based Ca-free materials, into which Cu may be incorporated according to this invention, contain, by weight %, the following, keeping in mind that one or more of the other trace elements may be included in addition to Cu in analogous concentrations, or instead of Cu:

TABLE 3

Wt. % Composition of Ca-Free Borate Glasses

| | $B_2O_3$ | $Na_2O$ | $Li_2O$ | MgO | BaO | CuO |
|---|---|---|---|---|---|---|
| I | 49.0 | 14.6 | | | 36.1 | 0.3 |
| II | 78.7 | | 11.1 | 10.0 | | 0.2 |
| III | 78.7 | | 11.1 | | 10.0 | 0.2 |
| IV | 75.8 | | 11.0 | | 13.0 | 0.2 |
| V | 58.7 | | 8.0 | | 33.0 | 0.3 |
| VI | 45.0 | | 6.6 | | 48.0 | 0.4 |
| VII | 69.7 | | 10.0 | 10.0 | 10.0 | 0.3 |

In certain embodiments of the invention, the biocompatible material is selected to include at least two of the alkali oxides $Li_2O$, $Na_2O$, $K_2O$, and/or $Rb_2O$ in a cumulative concentration of between about 5 and about 25 wt %, such as between about 8 and 20 wt %. It has been discovered to be advantageous to include two or more such alkali compounds in order to reduce the tendency for crystallization, which ultimately improves the workability and manufacturability of the glasses, which can important to making scaffolds. Using more than one type of alkali (i.e., mixed alkali) can reduce the cost of a glass, modify its reaction rate with body fluids, and provide additional elements beneficial to tissue growth and regeneration.

A further feature of certain embodiments is that the cumulative concentration of the alkaline earth oxides from the group consisting of MgO, SrO, BaO, CaO, and combinations thereof is in the range of 1 to about 50 wt %, such as in the range of 1 to 30 wt %, or even about 8 to 25 wt %. Certain of these embodiments contain two or more such alkaline earth oxides in a range of 1 to 45 wt % cumulatively, such as in the range of 5 to 25 wt %. If SrO is present in a concentration which yields a Sr concentration above 10 wt %, it does not qualify as a trace element in accordance with this invention.

These embodiments into which Cu and/or other trace element may be incorporated and which employ mixed alkali oxide contents contain $B_2O_3$ from about 40 to about 80 wt %. Certain of these embodiments consist essentially of $B_2O_3$ from about 40 to about 80 wt %, mixed alkali oxides selected from the group consisting of $Li_2O$, $Na_2O$, $K_2O$, and $Rb_2O$, and one of MgO, SrO, BaO, or CaO, plus the Cu containing compound. Other embodiments consist essentially of $B_2O_3$ from about 40 to about 80 wt %, two or more alkali oxides selected from the group consisting of $Li_2O$, $Na_2O$, $K_2O$, and $Rb_2O$, and two or more alkaline earth oxides from the group consisting of MgO, SrO, BaO, and CaO, plus the Cu containing compound. For example, composition A in Table 2 consists essentially of $B_2O_3$ from about 40 to about 80 wt %, two or more mixed alkali oxides selected from the group consisting of $Li_2O$, $Na_2O$, $K_2O$, and $Rb_2O$ in a cumulative wt % between 5 and 25%, and two or more from among MgO, SrO, BaO, and CaO in a cumulative wt % between 8 and 25%. Other embodiments optionally include one or more of $P_2O_5$, $SiO_2$, $Al_2O_3$, F, and transition metal elements.

The invention includes incorporating Cu and/or other trace element into biocompatible materials with an especially high $B_2O_3$ composition, namely, from about 60 to about 82 wt %, still more preferably from about 70 to about 80 wt %. These embodiments employ an alkali oxide selected from the group consisting of $Li_2O$, $Na_2O$, $K_2O$, $Rb_2O$, and combinations thereof cumulatively from about 1 to about 50 wt %, such as from about 5 to about 25 wt %, and even from about 8 to about 20 wt %; and even optionally two or more such oxides cumulatively in this range. They also optionally employ alkaline earth oxides from group consisting of MgO, SrO, BaO, CaO, and combinations thereof in the range of about 1 to about 50 wt %, such as in the range of 1 to 30 wt %, or even about 8 to 25 wt %, and even two or more such oxides cumulatively in this range. Certain of these embodiments consist essentially of these components, such as compositions II, III, IV, and VII in Table 3; while other embodiments optionally include one or more of $P_2O_5$, $SiO_2$, $Al_2O_3$, F, and transition metal elements.

In the foregoing described mixed-alkali and high-borate embodiments, the Ca concentration may be strictly controlled to less than about 5 wt %, including to less than 0.5 wt %, such as to less than 0.2 wt % or less than 0.1 wt % to avoid the formation of Ca compounds, in the manner discussed above. Alternatively, there are embodiments containing two or more alkali oxides which also contain CaO in an amount up to about 40 wt % to facilitate the formation of hydroxyapatite, other calcium phosphate compounds, amorphous calcium phosphate, or other calcium containing compounds.

Some exemplary materials of the invention such as depicted in the working examples contain, approximately, 40 to 80 wt % $B_2O_3$, 0.05 to 5% CuO, and $Na_2O$, $K_2O$, MgO, and $P_2O_5$. More specific examples contain or even consist essentially of 40 to 80 wt % $B_2O_3$, 0.1 to 5% CuO, 1 to 25 wt % $Na_2O$, 1 to 25 wt % $K_2O$, 1 to 25 wt % MgO, and 1 to 10 wt % $P_2O_5$.

The invention also encompasses a biocompatible composition for implantation into a mammal to facilitate vessel growth in repair, regeneration, and/or proliferation of bodily tissue, wherein the biocompatible material is phosphate-based or silicate-based and is at least partially dissolvable in mammalian bodily fluids, and Cu is incorporated into the biocompatible material in a concentration as described above. In these embodiments, $P_2O_5$ and/or $SiO_2$ are glass formers and constitute about 20 to about 65 wt % $P_2O_5$ or about 20 to about 60 wt % $SiO_2$. These materials also contain an alkali metal oxide component of, for example, one or more of $Li_2O$, $Na_2O$, $K_2O$, $Rb_2O$, $Cs_2O$, or a mixture thereof in a concentration of about 8 wt % to about 55 wt %, such as about 10 to about 52 wt %. Many of these phosphate- and silicate-based glasses also contain a calcium component, one of CaO, $CaF_2$, or mixtures thereof. For example, many of these glasses contain from about 5 to about 40 wt % of CaO or $CaF_2$, or mixtures thereof, such as about 10 to about 30 wt % of CaO or $CaF_2$, or mixtures thereof, or about 10 to about 15 wt % of CaO or $CaF_2$, or mixtures thereof. Accordingly, one of these embodiments contains about 20 to about 65 wt % $P_2O_5$, and one or more of $Li_2O$, $Na_2O$, $K_2O$, $Rb_2O$, $Cs_2O$, or a mixture thereof in a concentration of about 8 wt % to about 55 wt %, and a calcium component of in a concentration of about 5 to about 40 wt % of CaO or $CaF_2$, and Cu in a concentration of about 0.05 to about 5 wt %, such as between about 0.1 and about 2.5 wt %. Another embodiment contains about 20 to about 65 wt % $P_2O_5$, and one or more of $Li_2O$, $Na_2O$, $K_2O$, $Rb_2O$, $Cs_2O$, or a mixture thereof in a concentration of about 10 wt % to about 52 wt %, a calcium component of CaO or $CaF_2$ or mixtures thereof in a concentration of about 5 wt % to about 40 wt % of CaO or $CaF_2$ or mixtures thereof, and Cu in a concentration of about 0.05 to about 5 wt %, such as between about 0.1 and about 2.5 wt %. Another embodiment contains about 20 to about 65 wt % $P_2O_5$, and one or more of $Li_2O$, $Na_2O$, $K_2O$, $Rb_2O$, $Cs_2O$, or a mixture thereof in a concentration of about 8 wt % to about 55 wt %, a calcium component of CaO or $CaF_2$ or mixtures thereof in a concentration of about 10 to about 30 wt % of CaO or $CaF_2$ or mixtures thereof, and Cu in a concentration of about 0.05 to about 5 wt %, such as between about 0.1 and about 2.5 wt %. Another of these embodiments contains about 20 to about 60 wt % $SiO_2$, and one or more of $Li_2O$, $Na_2O$, $K_2O$, $Rb_2O$, $Cs_2O$, or a mixture thereof in a concentration of about 8 wt % to about 55 wt %, a calcium component of CaO in a concentration of about 5 to about 40 wt % of CaO or $CaF_2$, and Cu in a concentration of about 0.05 to about 5 wt %, such as between about 0.1 and about 2.5 wt %. Another embodiment contains about 20 to about 60 wt % $SiO_2$, and one or more of $Li_2O$, $Na_2O$, $K_2O$, $Rb_2O$, $Cs_2O$, or a mixture thereof in a concentration of about 10 wt % to about 52 wt %, a calcium component of CaO or $CaF_2$ or mixtures thereof in a concentration of about 5 wt % to about 40 wt % of CaO or $CaF_2$ or mixtures thereof, and Cu in a concentration of about 0.05 to about 5 wt %, such as between about 0.1 and about 2.5 wt %. Another embodiment contains about 20 to about 60 wt % $SiO_2$, and one or more of $Li_2O$, $Na_2O$, $K_2O$, $Rb_2O$, $Cs_2O$, or a mixture thereof in a concentration of about 8 wt % to about 55 wt %, a calcium component of CaO or $CaF_2$ or mixtures thereof in a concentration of about 10 to about 30 wt % of CaO or $CaF_2$ or mixtures thereof, and Cu in a concentration of about 0.05 to about 5 wt %, such as between about 0.1 and about 2.5 wt %. In certain of these embodiments, $CaF_2$ is strictly avoided and the calcium component is CaO.

Examples of silicate-based biocompatible material containing Cu and other trace elements in accordance with this invention are as follows:

TABLE 4

Weight Percent Composition of Silicate-Based Biocompatible Glasses (wt %)

| Glass | $SiO_2$ | $Na_2O$ | $P_2O_5$ | CaO | CuO | FeO | $CaF_2$ | $B_2O_3$ | ZnO | MnO | MgO | $K_2O$ |
|---|---|---|---|---|---|---|---|---|---|---|---|---|
| A | 44.6 | 24.3 | 5.9 | 24.3 | 1.0 | | | | | | | |
| B | 44.1 | 24.0 | 5.9 | 24.0 | 2.0 | | | | | | | |
| C | 43.7 | 23.8 | 5.8 | 23.8 | 3.0 | | | | | | | |
| D | 43.2 | 23.5 | 5.8 | 23.5 | 4.0 | | | | | | | |
| E | 42.8 | 23.3 | 5.7 | 23.3 | 5.0 | | | | | | | |
| F | 44.0 | 25.0 | 6.0 | 20.0 | 0.2 | 0.2 | 1.0 | 2.2 | 0.6 | 0.2 | 0.6 | |
| G | 50.0 | 6.0 | | 19.0 | 0.2 | 0.2 | 1.0 | 3.0 | 1.0 | 0.2 | | 12.0 |

Examples of phosphate-based biocompatible glass contain Cu in accordance with this invention are shown in Table 5.

TABLE 5

Weight Percent Composition of Phosphate-Based Biocompatible Glasses

| Glass ID | $Na_2O$ | $K_2O$ | CaO | MgO | $B_2O_3$ | $P_2O_5$ | $Li_2O$ | SrO | CuO |
|---|---|---|---|---|---|---|---|---|---|
| P-1 | 3.8 | 5.8 | 27.5 | 2.5 | 0.0 | 60.0 | 0.0 | 0.0 | 0.4 |
| P-2 | 9.2 | 9.3 | 27.5 | 0.0 | 0.0 | 53.5 | 0.0 | 0.0 | 0.5 |
| P-3 | 7.8 | 11.8 | 17.0 | 7.6 | 0.0 | 55.2 | 0.0 | 0.0 | 0.6 |
| P-4 | 7.8 | 11.8 | 17.0 | 7.6 | 0.0 | 55.2 | 0.0 | 0.0 | 0.6 |
| P-5 | 6.6 | 8.9 | 21.9 | 0.0 | 4.1 | 58.0 | 0.0 | 0.0 | 0.5 |
| P-6 | 10.5 | 0.0 | 23.0 | 0.0 | 4.0 | 61.1 | 1.1 | 0.0 | 0.3 |
| P-7 | 8.0 | 3.7 | 1.5 | 0.0 | 1.8 | 78.1 | 0.0 | 6.7 | 0.2 |

These phosphate-based formulations demonstrate situations where it is advantageous to include at least two of the alkali oxides $Li_2O$, $Na_2O$, $K_2O$, and/or $Rb_2O$ in a cumulative concentration of between about 5 and about 25 wt %, such as between about 8 and 20 wt %. As noted above, it has been discovered to be advantageous to include two or more such alkali compounds in order to reduce the tendency for crystallization, which ultimately improves the workability and manufacturability of the glasses, which can be important to making scaffolds. Using more than one type of alkali (i.e., mixed alkali) can reduce the cost of a glass, modify its reaction rate with body fluids, and provide additional elements beneficial to tissue growth and regeneration.

A further feature of these phosphate-based embodiments is that the cumulative concentration of the alkaline earth oxides from the group consisting of MgO, SrO, BaO, CaO, and combinations thereof is in the range of 1 to about 50 wt %, such as in the range of 1 to 30 wt %, or even about 8 to 25 wt %. Certain of these embodiments contain two or more such alkaline earth oxides in a range of 1 to 45 wt % cumulatively, such as in the range of 5 to 25 wt %.

The biocompatible materials of the invention are in the form of solid fibers, hollow fibers, ribbons, solid spheres, hollow spheres, particles, and combinations thereof. In an especially preferred embodiment for many applications, the composition is in the form of a scaffold body which includes fibers, and in certain such embodiments it is a scaffold body which consists essentially of components which are fibers. The fibers have an aspect ratio of at least 2:1 length:transverse dimension (e.g., diameter), and more typically at least 5:1, such as greater than 10:1. In certain embodiments of the invention, the scaffold body components are primarily one form, such as fibers, in combination with a minor constituent of a second form from the foregoing options, such as microspheres.

There is also an option with this invention of employing distinct component compositions to strategically impart certain properties. For example, the composition in some embodiments of the composition employs 10 to 90 wt % of components having one composition selected from the above, and 10 to 90 wt % of components of a different composition. Or even more than two such types of components may be employed. That is, the material may contain at least 10 wt % of components comprising a first component material within the contemplated compositions and at least 10 wt % of components comprising a second component material, wherein the first and second component materials have compositions measurably distinct from each other. And it is contemplated that only the first component material may contain Cu and/or other trace element, or that Cu may be present in both materials in different amounts. This permits the selection of, for example, faster reacting fibers in combination with slower reacting fibers; or the selection of Ca-containing fibers with Ca-free fibers. One can therefore select standard composition components and combine them with non-standard composition components to effectively customize or dope the scaffold for the application presented, or for the host's particular needs. Alternatively, hollow spheres containing a growth factor or drug for delivery to the host can be incorporated with other structural components, such as fibers.

In one embodiment the Cu and/or other trace element is incorporated into the materials and a scaffold is formed to have a porosity which is selected to provide fluid flow into the scaffold to facilitate uptake of bodily fluids, while maintaining sufficient strength for handling and implantation. The porosity is between about 15 vol % and about 90 vol %. There are different levels of porosity, for example between about 15 and about 30 vol %, or between about 30 and about 60 vol %, or between about 60 and about 90%, which are preferred for different applications. Porosity depends on or is controlled by many factors such as fiber orientation, shape of particles or microspheres, and the thermal treatment (time/temperature) used to bond the elements together. Independent of this bulk porosity, interconnectivity is also important in embodiments of the invention which are in the form of scaffolds. Because tissue repair is strongly influenced by flow of bodily fluids into the scaffold, it is preferred to have a high level of interconnectivity of pores within the scaffold, and a low level of closed pores. That is, it is important that most pores be connected to other pores, and that there is a direct or indirect path from most pores to the exterior surface of the scaffold. In certain embodiments, at least about 80 vol %, such as at least about 90%, of the pore volume of the scaffold is directly or indirectly through other pores accessible from the scaffold exterior, and therefore accessible to bodily fluids.

The method of making the biocompatible materials is not narrowly critical to the invention. By way of example, in preparing the biocompatible materials, individual analytical reagent grade components are weighed, mixed thoroughly, and melted in a platinum crucible at temperatures between 1000 to about 1500° C., depending upon composition for approximately one to four hrs. The melt is then quenched, for example, on a steel or copper plate to form glass that can be ground into particulates of a desired size. The particulates can be spheroidized to form microspheres of a chosen diameter. The material of preferred composition when in the form of a melt can easily be formed into fibers. If fibers of the borate glass are made, they can either be pulled by hand directly from the melt or pulled through bushing by a rotating drum.

The components can be self bonded to form three dimensional scaffolds by simply heating an assemblage of particulates in a furnace and allowing the fibers/particles/spheres to soften and bond to each other. After the allotted time at temperature, the construct is removed from the furnace and cooled to room temperature. Many prior biocompatible glasses, such as 45S5, are difficult to self bond due to crystallization of the glass. Therefore the self-bonding ability of the borate glasses comprising Cu is a distinct advantage over other biocompatible materials currently in use.

In one embodiment of the invention employing the Cu-containing biocompatible materials the Cu-containing materials are in the form of a tissue scaffold prepared from fibers which are aligned so that a majority of the fibers are substantially aligned in a parallel direction. The scaffold is prepared by placing and orienting fibers in a unidirectional manner in a mold. The fibers in the mold are heated to a temperature where the fibers soften and bond together. In one preferred embodiment, the fibers are self bonded in the sense that no adhesive, braze, or other external bonding agent is used for bonding. An alternative embodiment employs a biocompatible agent or adhesive to facilitate bonding, such that the fibers are not self bonded, at least in part. Upon cooling, the assemblage of bonded fibers is sufficiently rigid and strong that the assemblage can be removed from the mold and handled. The scaffold is sufficiently rigid that it can be implanted into a mammal where it facilitates the repair and regeneration of hard tissue such as bone (including cortical and cancellous) or soft tissue such as muscle, cartilage, skin, organ, or other hard or soft tissue.

The orientation of the fibers in a lengthwise direction in the self-bonded scaffold provides lengthwise channels (or connected pores) among the fibers, which channels provide for uptake into the scaffold of stem cells, growth factors, medicines, red blood cells and other bodily fluids and components carried in bodily fluids. The fibers are arranged to define channels within the scaffold which facilitate fluid flow into and lengthwise within the scaffold from one end to the other end. The orientation also provides for channels in a transverse direction generally perpendicular to the lengthwise direction of the oriented fibers, to facilitate uptake of fluids from the outer surface of the interior or core of the scaffold. These longitudinal and transverse channels exert significant capillary forces on a liquid which cause the liquid to be drawn into the scaffold. This capillary action facilitates the distribution of these fluids and components relatively uniformly through the scaffold and enables fluids to flow from one end of the scaffold to the other or to enter the scaffold from its surface and transmit the liquid to its ends.

The invention in one embodiment employs fibers having a diameter, prior to molding and softening, between about 20 and about 5000 microns, such as between about 50 and about 5000 microns. In one embodiment the scaffold is prepared from fibers having diameters between about 100 and about 450 microns, such as between about 100 and about 300 microns. In an alternative embodiment, the scaffold is prepared from fibers having diameters up to about 3000 or 5000 microns (3 to 5 mm), which can be deemed more akin to rods than fibers in some contexts, but for purposes of the discussion of this invention fall within the definition of "fibers."

In one aspect of the invention employing co-aligned fibers, at least about 75 or 85% by volume of the fibers in the scaffold are longitudinally co-aligned. In this regard the fibers are co-aligned longitudinally, where "co-aligned longitudinally" and the like phrases (e.g., "in lengthwise co-alignment") as applied to a group of adjacent, bundled, or joined fibers in this application means that the alignment of each fiber in the group at any one place along at least about 75% of its length does not deviate more than about 25 degrees from parallel to the central axis of the scaffold. In one preferred embodiment, each fiber in the group at any one place along at least about 75% of its length does not deviate more than about 15 degrees from parallel to the central axis of the scaffold. In another preferred embodiment, each fiber in the group at any one place along at least about 75% of its length does not deviate more than about 10 degrees from the central axis of the scaffold. So it is evident that this co-alignment aspect does not require 100% precise co-alignment of all fibers. The longitudinal co-alignment aspect also allows for some minor deviation of specific segments of individual fibers to an orientation outside these 25, 15, and 10 degree requirements. This is reflected in the requirement that the longitudinal co-alignment is of each fiber along at least 75% of its length, rather than necessarily along its entire length. So up to about 25% of the length of an individual fiber may be misaligned because, for example, it was bent during the scaffold-making process or otherwise. Each fiber in the scaffold is not absolutely straight, nor is it lying along an absolutely straight line strictly parallel to all other fibers in the scaffold. And each fiber is oriented generally in the same direction, but each is not oriented in exactly the same direction. Moreover, the scaffold itself in certain embodiments is curved, bent, or otherwise not straight, in which cases the central axis of the scaffold to which the alignment of the fibers is within 25 degrees of parallel is also curved, bent, or otherwise not straight. In certain embodiments a straight or curved scaffold is machined into a more complex shape, in which instance the scaffold central axis refers to the central axis as molded and prior to machining.

In order to allow capillary action and channel-forming, the scaffold theoretically contains at least three fibers, although the scaffold typically comprises dozens and even hundreds of fibers. The fibers lie generally lengthwise of the scaffold central axis A (i.e., lie generally in the direction of the central axis) and are generally free of helical orientation about the scaffold central axis. This arrangement applies to at least about 75 vol % of the fibers and preferably to substantially all of the fibers.

The aspect of this embodiment that the fibers are co-aligned longitudinally contemplates that the fibers are positioned so that they have a similar alignment, which similar alignment may be straight, bent, or curved. In most embodiments they are non-helical. In a separate and distinct aspect of certain preferred embodiments, this common alignment is limited to a generally straight alignment along at least about 75%, 85%, or 95% of the length of the fibers. In other words, at least about 75%, 85%, or 95% of each fiber is generally straight, i.e., at least about 75%, 85%, or 95% of the length of each fiber has an alignment which is within 10 degrees of a mean straight central axis for the fiber. So up to 5%, 15%, or 25% of the length of each fiber may be curved, bent, or otherwise deviate more than 10 degrees from straight in relation to the overall fiber length, but the rest of each fiber is generally straight in that it so deviates less than 10 degrees. In one preferred embodiment, substantially the entire length of each fiber is generally straight in that it deviates less than 10 degrees from the fiber's average central axis. The "mean straight central axis" is the imaginary central axis for the fiber which is absolutely straight and is an average of all axes along the fiber length.

The fibers in the scaffold of these embodiments are selected to have characteristics suitable for the specific application. In one embodiment, the fibers have a length between about 6 mm and about 150 mm, such as between about 12 mm and about 100 mm or between about 25 mm and about 75 mm. Each fiber has a length which is at least about 10 times its diameter. "Diameter" as used herein refers to the fiber's largest dimension transverse to its length, and it does not imply that the fibers are perfectly circular in cross section. Each fiber therefore has a fiber lengthwise dimension which is at least about 10 times the fiber transverse dimension, e.g., diameter. In one embodiment, the fiber length is selected so that all, substantially all, or at least about 85 vol % of the individual fibers extend the entire length of the scaffold. The fibers may be selected to have a pre-molding, pre-joining length which corresponds to the length of the scaffold. Or in most embodiments, the length of the fibers is longer than the desired ultimate scaffold length, and the scaffold is cut to the desired length after molding and joining. In an alternative embodiment, the length of a substantial portion (e.g., at least 40 vol %) or all of the fibers is significantly less than the entire length of the scaffold.

The scaffold in these embodiments is manufactured to have a sufficiently high open and interconnected porosity from end to end of the scaffold to facilitate capillary flow of fluids such as bodily fluids and medicines and components they carry through the length of the scaffold, as well as generally transverse from outside walls of the scaffold into the scaffold interior in directions generally transverse to the longitudinal dimension of the fibers. And the scaffold is manufactured so that the ultimate porosity is low enough that the scaffold has required strength for handling, implantation, and service after implantation. If the porosity is too high, the scaffold risks breakage in service, depending on where it is implanted and the loads it encounters. In a preferred embodiment, the porosity as measured in volume is between about 10% and about 35%, for example between about 10% and about 30%, or between about 10% and about 25%. The porosity is controllable mainly by controlling the degree of softening of the fibers, in that highly softened fibers fuse together more completely to a structure with lower porosity. The degree of softening and fusing is controlled by controlling the joining temperature and time. Porosity is also affected by the fiber diameter and by the range in fiber diameter within a given scaffold. Porosity tends to increase with an increasing range in fiber diameter.

The biocompatible material may be glassy, glass ceramic, or ceramic in nature. However the glassy state is preferred in this invention because, generally speaking, glassy materials are easier to form into different shapes, bond at lower temperatures and are more chemically homogeneous than their crystalline or partially crystalline counterparts of the same composition. It is therefore preferable that the biocompatible material is substantially glass in that less than about 5 wt %, more preferable less than 1 wt %, of the component material is crystalline material. More particularly, it is preferable that there is less than 5 wt %, preferably less than 1 wt %, crystallization when the material is heated to a temperature needed to bond the individual glass particles together. By way of example, in one embodiment it is preferable that there is less than 5 wt %, preferably less than 1 wt %, crystallization when the material is heated to 800° C. at an average heating rate of 20° C./min, held at that temperature for 10 minutes, then cooled to room temperature by exposure to STP conditions of room temperature and atmospheric pressure. More preferably, the glass will contain less than 5 wt % crystallization, even more preferably less than 1 wt % crystallization, after being heated to 575° C. with a ramp rate of 20° C./min, and held at that temperature for 20 minutes, then cooled to room temperature by exposure to STP conditions. The fibers used in many embodiments of the invention, consistent with the foregoing description, are at least 99 wt % an amorphous or non-crystalline solid, for example made by fusing a mixture of oxides such as one or more of $SiO_2$, $B_2O_3$, $P_2O_5$ (known as glass forming oxides) with basic oxides such as the alkali and alkaline earth oxides, along with the Cu compound. In an alternative embodiment, the fibers include glass ceramics fibers that contain both glassy and crystalline regions which in many respects function in the same manner as a fiber that is completely (100%) non-crystalline. It is acceptable in some applications if the glass fiber crystallizes during the bonding step. The fibers may alternatively be pre-reacted biocompatible glasses such as glass fibers pre-reacted for example to have a thin surface layer of hydroxyapatite.

EXAMPLE 1

Several borate-based glasses were prepared containing CuO in various amounts according to the following concentrations:

| | Trace Element Doped Borate Biocompatible Glasses (wt %) | | | | | | | | | |
|---|---|---|---|---|---|---|---|---|---|---|
| Glass | $B_2O_3$ | $Na_2O$ | CaO | $K_2O$ | MgO | $P_2O_5$ | CuO | SrO | ZnO | $Fe_2O_3$ |
| B3 | 53.00 | 6.00 | 20.00 | 12.00 | 5.00 | 4.00 | | | | |
| B3 Cu-1 | 52.95 | 5.99 | 19.98 | 11.99 | 5.00 | 4.00 | 0.10 | | | |
| B3 Cu-2 | 52.89 | 5.99 | 19.96 | 11.98 | 4.99 | 3.99 | 0.20 | | | |
| B3 Cu-3 | 52.79 | 5.98 | 19.92 | 11.95 | 4.98 | 3.98 | 0.40 | | | |
| B3 Cu-4 | 52.47 | 5.94 | 19.80 | 11.88 | 4.95 | 3.96 | 1.00 | | | |
| B3 Cu-5 | 51.94 | 5.88 | 19.60 | 11.76 | 4.90 | 3.92 | 2.00 | | | |
| G | 51.73 | 5.86 | 19.52 | 11.71 | 4.88 | 3.90 | 0.40 | 2.00 | | |
| H | 51.20 | 5.80 | 19.32 | 11.59 | 4.83 | 3.86 | 0.40 | 2.00 | 1.00 | |
| I | 50.88 | 5.76 | 19.20 | 11.52 | 4.80 | 3.84 | 0.40 | 2.00 | 1.00 | 0.40 |

Scaffolds prepared from glasses A, B, C, D, E, and F, which are depicted in FIG. 1, were implanted subcutaneously in the backs of rats, for selected time periods, and examined for vascularization. The rats were Fisher 344 rats having an age between 9 and 11 weeks and a weight between 200 and 300 grams. Prior to implantation, the scaffolds were washed twice with ethyl alcohol and heat sterilized at 250° C. for 2.5 hours in a small box furnace. For implantation, the back of the rat was shaved, sterilized with iodine, and washed with 70% ethanol. Each rat was anesthesized with a mixture of isofluorine and medical grade oxygen. Implantation was subcutaneously in a pocket formed in the back of each rat. Each pocket was sufficiently large to ensure that each scaffold could be inserted away from the incision site. The incisions were closed with super glue (Krazy® Glue, Elmers Products inc. Columbus, Ohio). After implantation, 0.1 mL of Penicillin G Procaine was injected into each thigh of the rat to prevent infection. The rats were placed on a heating pad in a cage with fresh air during recovery.

Figure 2:
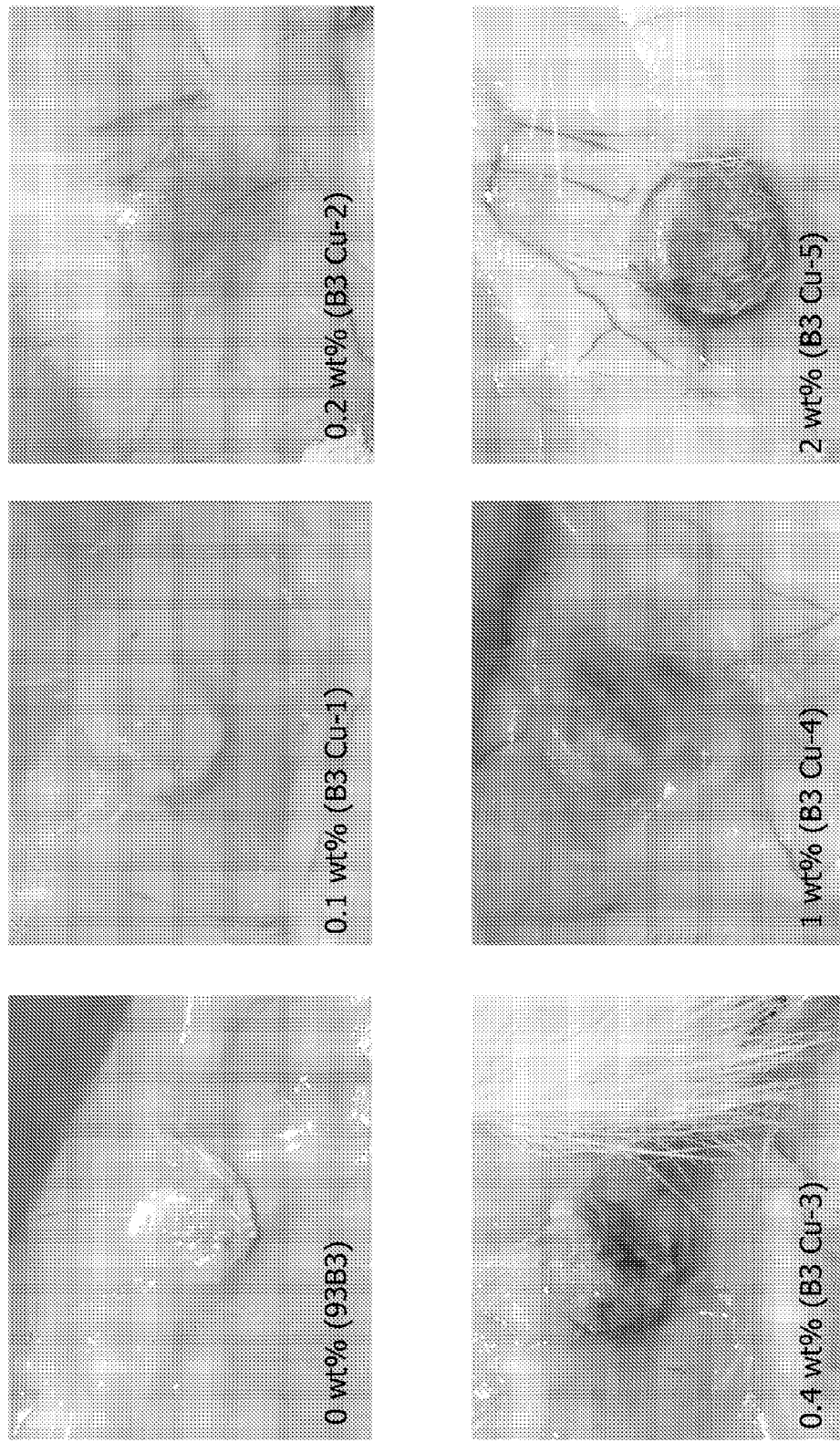
FIGS. 2, 3, and 4 each contain a series of photographs of scaffolds of FIG. 1 after implantation.
Figure 3:
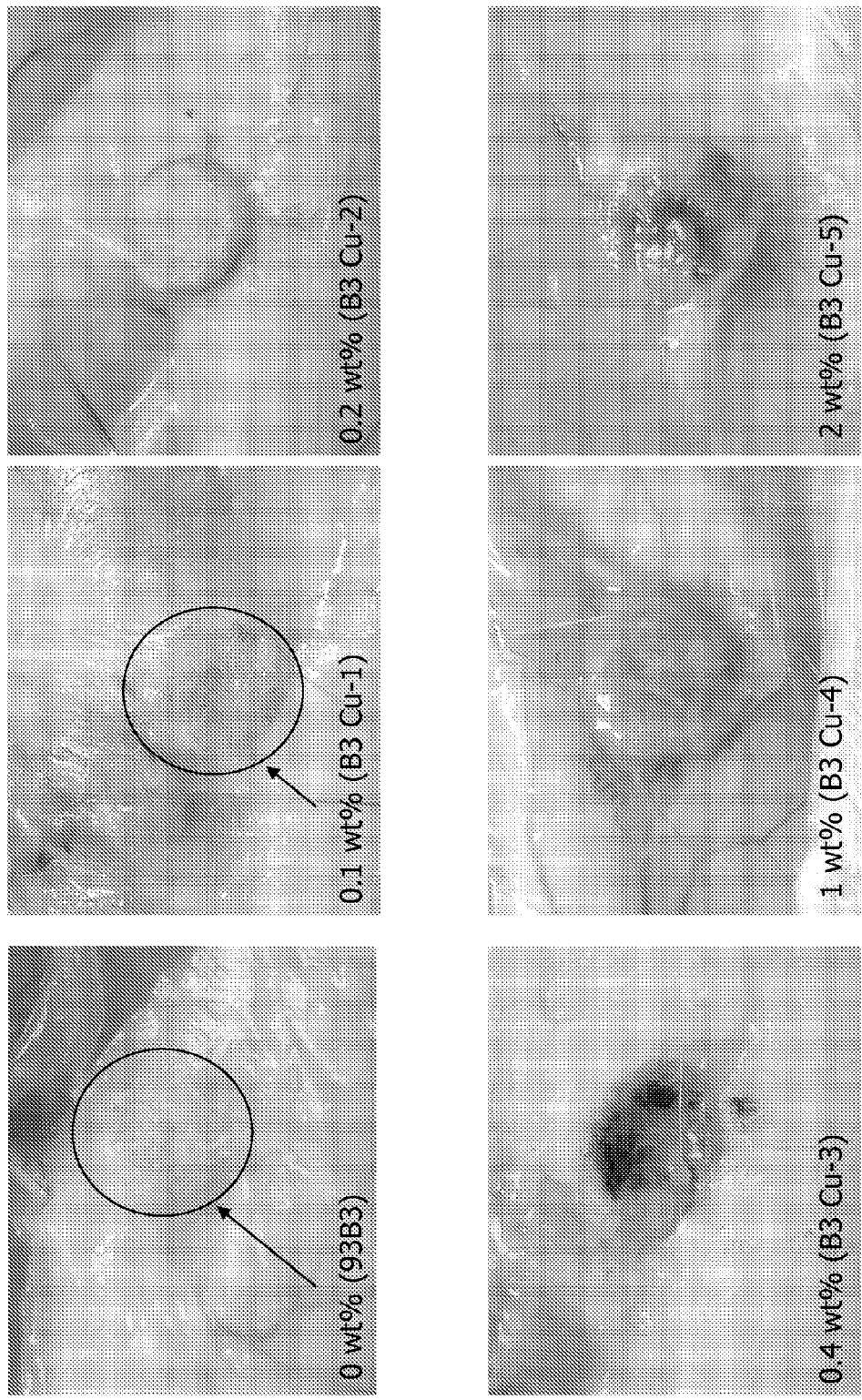
Figure 4:
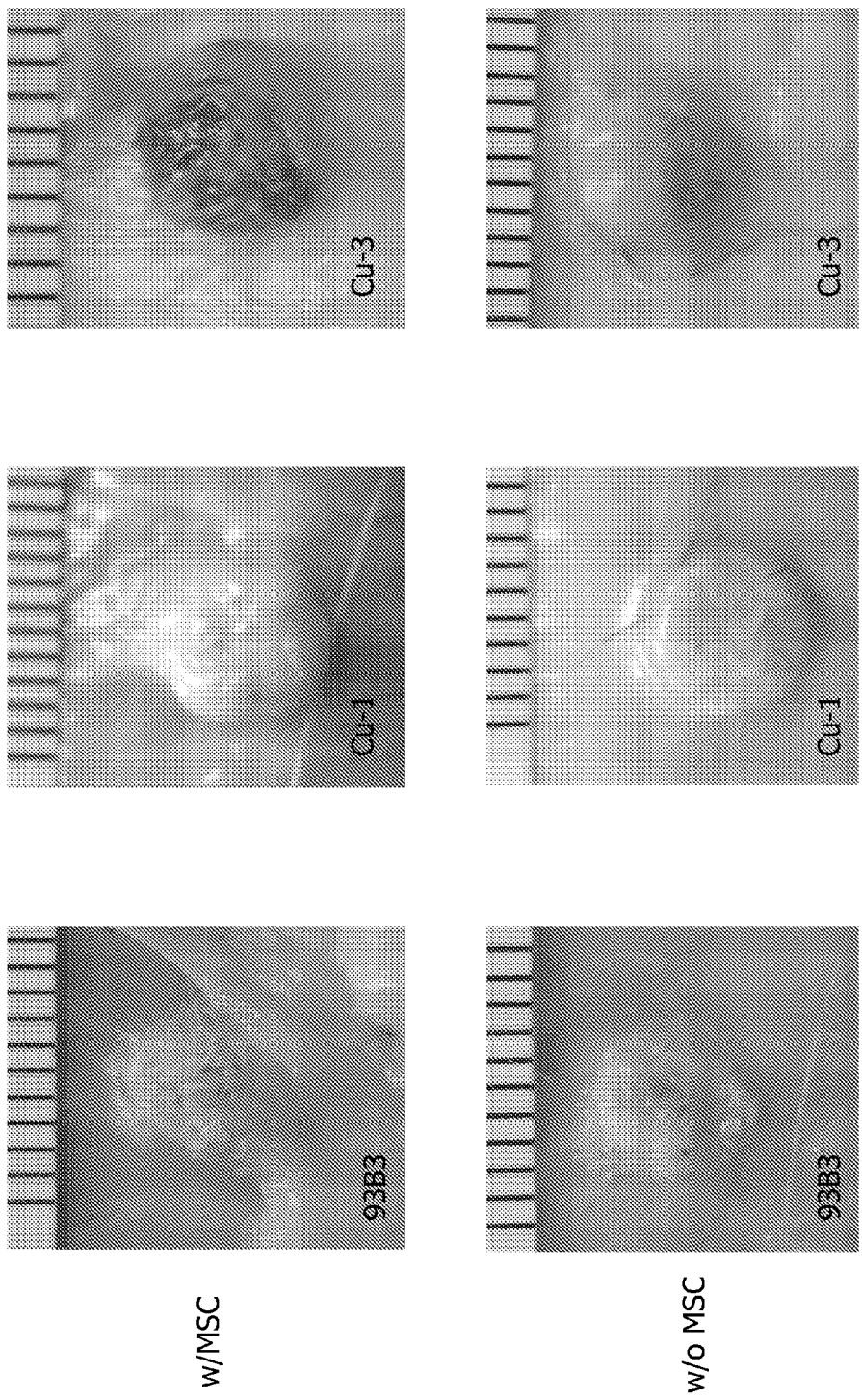

FIG. 2 shows the implanted scaffolds after two weeks; and FIG. 3 shows the implanted scaffolds after four weeks. FIG. 4 shows the implanted scaffolds of B3 (no Cu), B3 Cu-1 (0.1 wt % CuO), and B3 Cu-3 (0.4 wt % CuO) after six weeks. The designation "w/MSC" refers to scaffolds seeded with 50,000 mesenchymal stem cells (msc), and "w/o MSC" designates no seeding. The effect of increasing Cu content on increasing vascularization was evident.

EXAMPLE 2

Figure 5:
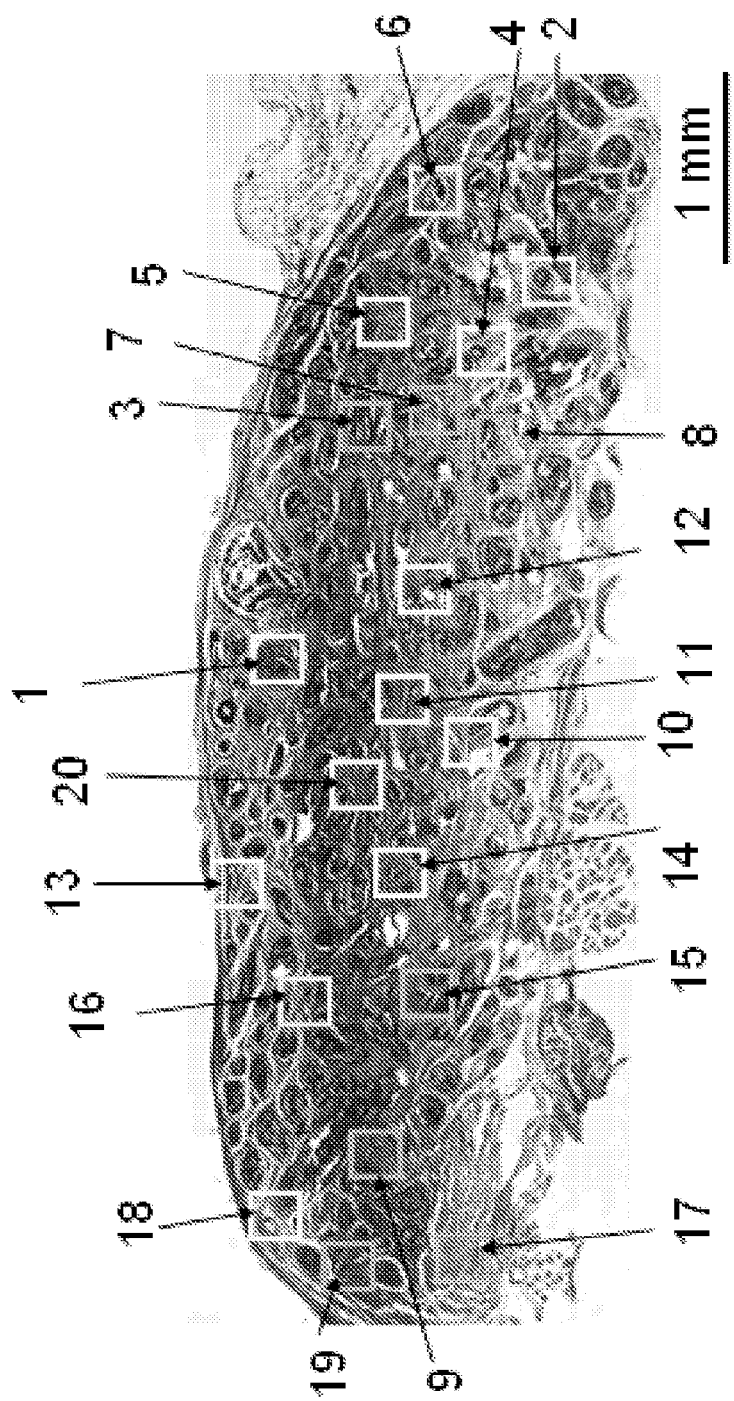
FIGS. 5 through 7 are photographs of scaffolds after implantation, removal, sectioning, and staining for histology (H&E).
Figure 6:
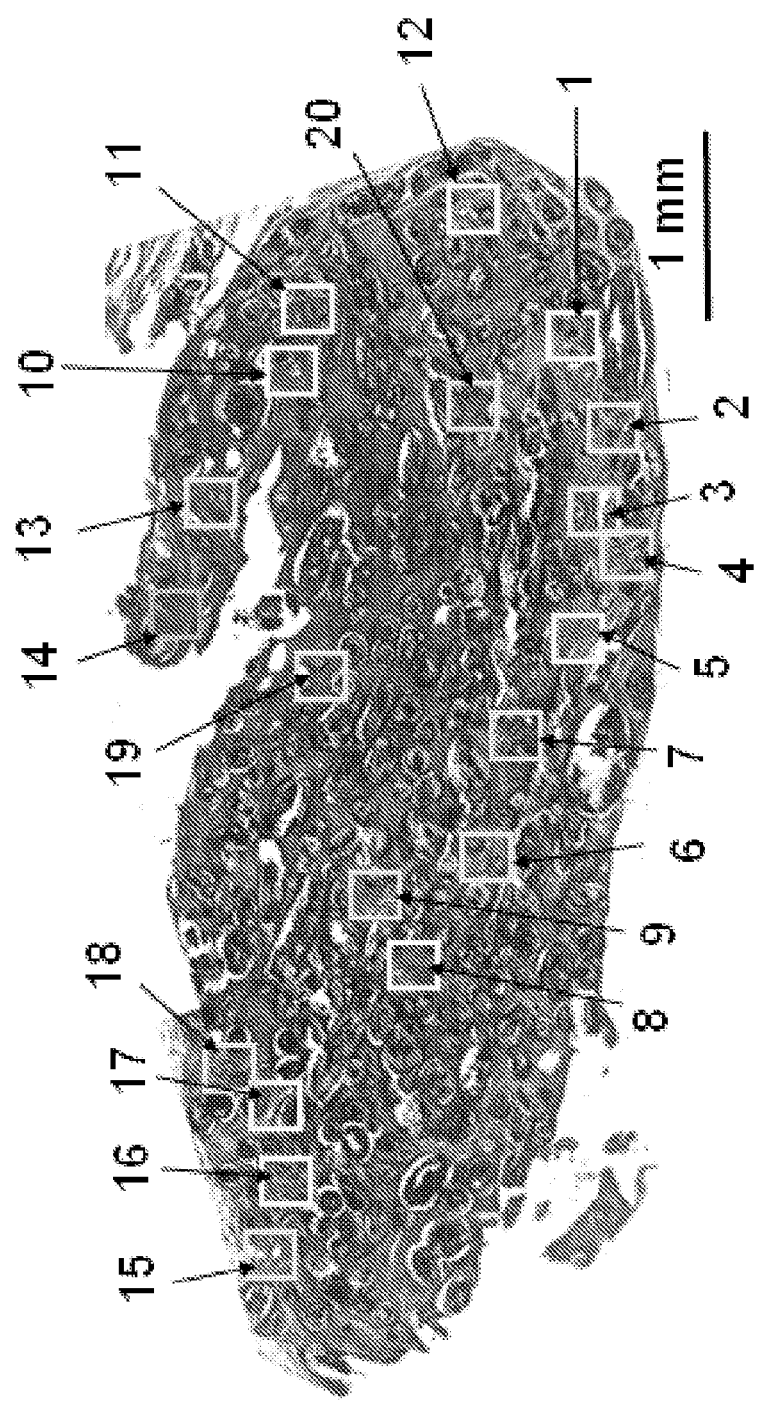
Figure 7:
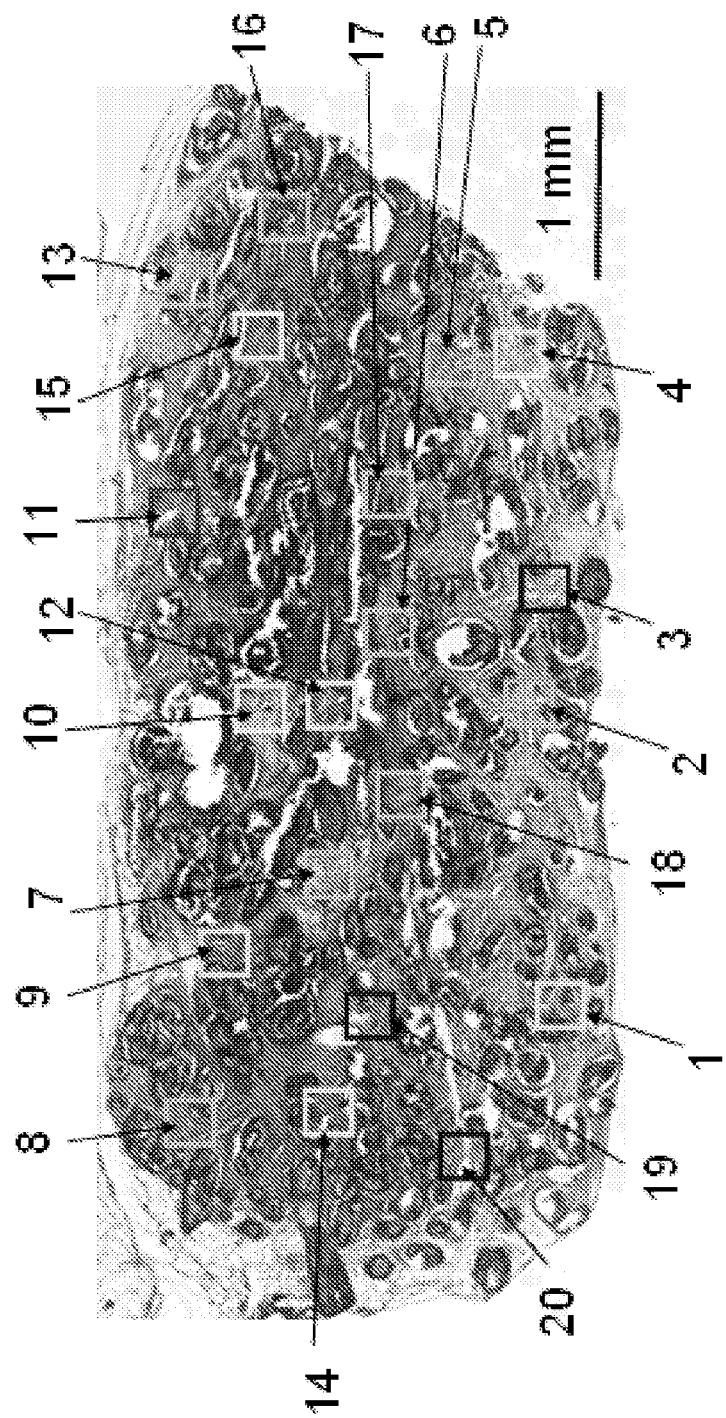
Figure 8:
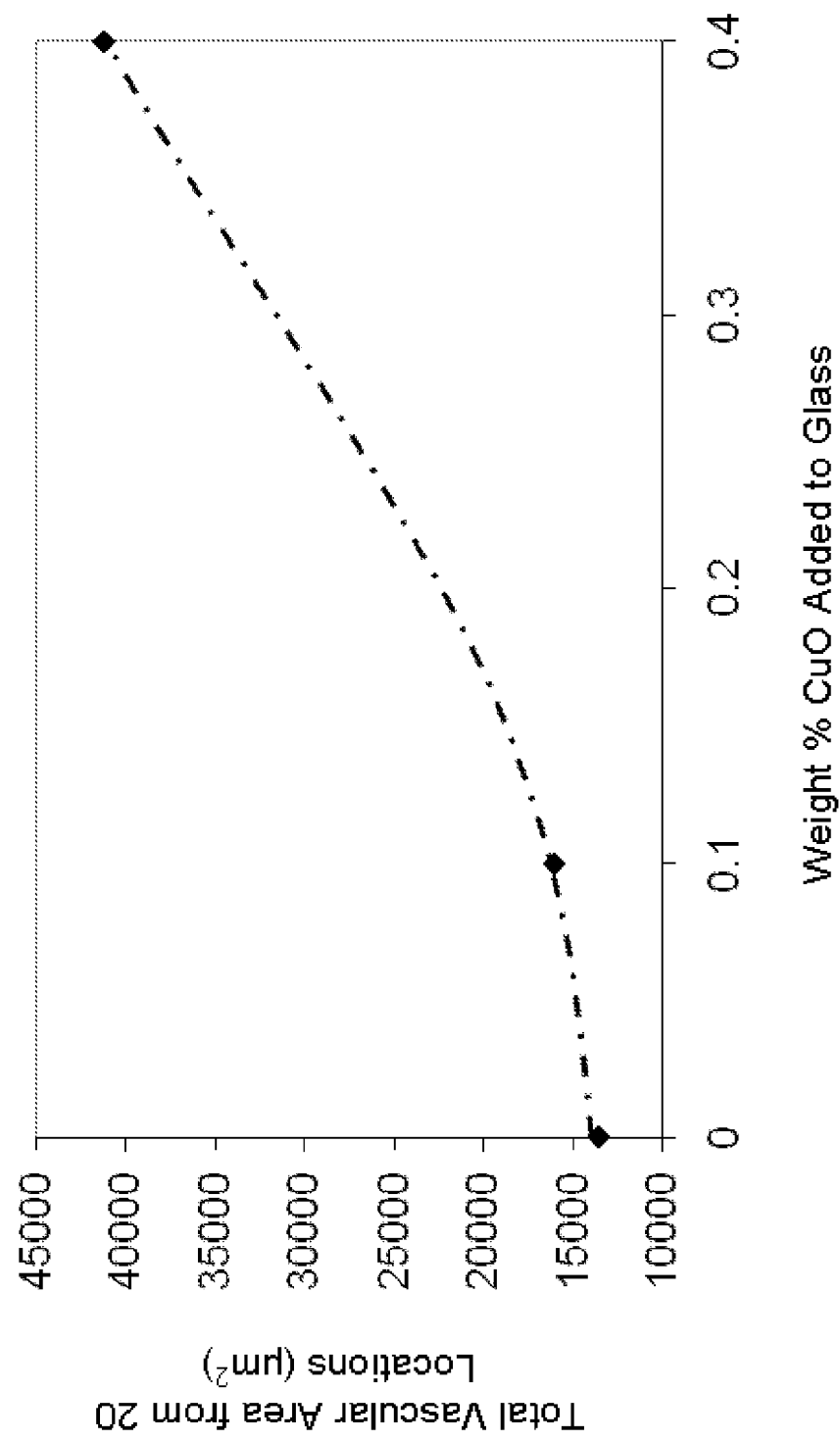
FIG. 8 is a graph depicting angiogenesis as a function of CuO content in biocompatible materials of the invention.

The scaffolds seeded with 50,000 mesenchymal stem cells (msc) were analyzed after removal from the rat. The scaffolds were sectioned and stained for histology (H&E). The degree of vessel formation was determined in 20 randomly selected spots throughout the sections, as indicated by the boxes in FIG. 5 (B3; no CuO), FIG. 6 (B3 Cu-1; 0.1 wt % CuO), and FIG. 7 (B3 Cu-3; 0.4 wt % CuO). FIG. 8 is a graph comparing total vascular area as a function of CuO concentration in the glass. The glass containing no CuO had a total of 14000 $\mu m^2$ vascular area; the glass containing 0.1% CuO had a total of 16000 $\mu m^2$ vascular area; and the glass containing 0.4% CuO had a total of 40000 $\mu m^2$ vascular area. There was a nearly 300% increase in vascular area in comparing the glass containing 0.4% CuO to the glass containing no CuO.

EXAMPLE 3

Copper trace element release rates were calculated for the B3 Cu-3 (0.4 wt % CuO) and B3 Cu-1 (0.1 wt % CuO) glasses. The scaffold mass was 70 mg (0.070 g). So the scaffold having 0.4 wt % CuO contained 0.00028 g CuO/scaffold, which is equivalent to 0.00022 g Cu/scaffold. The number of moles Cu was calculated as 0.00022 g/(63.55 g/mole), which equals 3.52E-6 moles Cu. Assuming six weeks (42 days) for the scaffold to completely react, the rate of dissolution was 3.52E-6 moles Cu in 42 days, which means 8.387E-8 moles of Cu was released or dissolved from the glass per day. The amount of new tissue grown was measured to be 0.05 g tissue/scaffold. Based on Amer. J. Phys. 214, 1968, the blood flow rate through adipose tissue of unanesthesized rats was a minimum of 0.1 and to a maximum of 0.4 ml/min/gram of tissue.

B3 Cu-3 (0.4 wt % CuO)

The scaffold having 0.4 wt % CuO contained 0.00028 g CuO/scaffold, which is equivalent to 0.00022 g Cu/scaffold. The number of moles Cu was calculated as 0.00022 g/(63.55 g/mole), which equals 3.52E-6 moles Cu. Assuming a linear reaction rate over 42 days for the scaffold to completely release all copper, the Cu release rate was 8.387E-8 moles/day. This is equivalent to 1.2E-6 moles of Cu/gram of glass/day.

B3 Cu-1 (0.1 wt % CuO)

Using a similar calculation for the B3 Cu-1 scaffold, the calculated release rate for copper was 2.095E-8 moles/day. The equivalent rate is 3.0E-7 moles of Cu/gram of glass/day.

The blood flow rates in rat subcutaneous adipose tissue have been measured between 0.1 and 0.4 ml/min/gram and reported by Herd et. al. in *Blood flow rates through adipose tissue of unanesthetized rats*. American journal of physiology, 1968. 214: p. 263-268. Using the Cu release rates for the B3 Cu-1 and B3 Cu-3 scaffolds described above, the Cu concentrations of the rat bodily fluids were calculated. The calculated values for the Cu concentration in the rat bodily fluids were in the range of Cu concentration of Cu doped cell culture mediums that promoted endothelial cell proliferation in-vitro reported by Hu et. al. in *Copper Stimulates Proliferation of Human Endothelial Cells Under Culture*. Journal of Cellular Biochemistry, 1998. 69: p. 326-335 and increased endothelial cell migration rates in-vitro reported as reported by McAuslan et al. in *Endothelial Cell Phagokinesis in Response to Specific Metal Ions*. Experimental Cell Research, 1980. 130: p. 147-157.

For the 0.4 wt % CuO scaffold at the minimum blood flow rate, the liters of flow through the scaffold was calculated as follows: 1440 min/day (0.1 ml/min*g)(1 day) (0.05 g)=7.2 ml=0.0072 L. Since there was a daily release of Cu of 8.387E-8 moles into a blood flow of 0.0072 L, the rate of Cu release was calculated as 8.387E-8 moles/day Cu/0.0072 L=1.165E-5 mol/L=11.65 micromolar Cu.

For the 0.4 wt % CuO scaffold at the maximum blood flow rate (4×0.0072 L=0.0288 L), the rate of Cu release was calculated as 8.387E-8 moles/day Cu/0.0288 L=2.91 E-6 mol/L=2.91 micromolar Cu.

For the 0.1 wt % CuO scaffold at the minimum blood flow rate (0.0072 L), the rate of Cu release was calculated as 2.095E-8 moles/day Cu/0.0072 L=2.91E-6 mol/L=2.91 micromolar Cu.

For the 0.1 wt % CuO scaffold at the maximum blood flow rate (4×0.0072 L=0.0288 L), the rate of Cu release was calculated as 2.095E-8 moles/day Cu/0.0288 L=7.3E-7 mol/L=0.73 micromolar Cu.

EXAMPLE 4

A blended fiber scaffold was prepared from a 50:50 by weight mixture of fibers of two or more distinct compositions:

| Glass | Fiber Content (wt %) | $B_2O_3$ | $Na_2O$ | CaO | $K_2O$ | MgO | $P_2O_5$ | CuO |
|---|---|---|---|---|---|---|---|---|
| Glass A | 50 | 53.00 | 6.00 | 20.00 | 12.00 | 5.00 | 4.00 | 0.0 |
| Glass B | 50 | 52.47 | 5.94 | 19.80 | 11.88 | 4.95 | 3.96 | 1.00 |

In view of the above, it will be seen that the several objects of the invention are achieved and other advantageous results attained.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above compositions and methods without departing from the scope of the invention, it is intended that all matter contained in the above description and shown in the accompanying drawings shall be interpreted as illustrative and not in a limiting sense.

The invention claimed is:

1. A scaffold for implantation into a mammal to facilitate vessel growth in repair, regeneration, and/or proliferation of bodily tissue, the scaffold comprising:
   a scaffold body of biocompatible material in a physical form selected from the group consisting of fibers, hollow fibers, tubes, ribbons, solid spheres, hollow spheres, particles, bonded particles, and combinations thereof which define a scaffold body having a weight between 10 milligrams and 500 grams, compressive strength greater than 0.4 mPa, and a surface area/bulk volume of between about 50 cm$^{-1}$ and about 1000 cm$^{-1}$;
   wherein the scaffold body has a porosity between about 15 and about 90 vol. % to provide fluid flow into the scaffold for uptake of bodily fluids;
   wherein the biocompatible material comprises from 50 to about 80 wt % $B_2O_3$; and
   wherein the biocompatible material comprises Cu in a concentration between about 0.05 and 10 wt % chemically dissolved in the biocompatible material.

2. The scaffold of claim 1 wherein the biocompatible material comprises:
   one or more alkali oxides selected from the group consisting of $Li_2O$, $Na_2O$, $K_2O$, and $Rb_2O$; and
   one or more alkaline earth oxides selected from the group consisting of MgO, SrO, BaO, and CaO.

3. The scaffold of claim 1 wherein the biocompatible material comprises:
   from about 1 to about 50 wt % of one or more alkali oxides selected from the group consisting of $Li_2O$, $Na_2O$, $K_2O$, and $Rb_2O$; and
   from about 1 to about 50 wt % of one or more alkaline earth oxides selected from the group consisting of MgO, SrO, BaO, and CaO.

4. The scaffold of claim 1 wherein the biocompatible material comprises:
   from about 5 to about 20 wt % of one or more alkali oxides selected from the group consisting of $Li_2O$, $Na_2O$, $K_2O$, and $Rb_2O$; and
   from about 5 to about 40 wt % of one or more alkaline earth oxides selected from the group consisting of MgO, SrO, BaO, and CaO.

5. The scaffold of claim 1 wherein the biocompatible material comprises:
   one or more alkali oxides selected from the group consisting of $Li_2O$, $Na_2O$, $K_2O$, and $Rb_2O$;
   one or more alkaline earth oxides selected from the group consisting of MgO, SrO, BaO, and CaO; and
   Cu in a concentration between about 0.1 and about 2.5 wt %.

6. The scaffold of claim 1 wherein glass formers in the biocompatible composition are concentration balanced to impart a biodegradability such that at least about 20 wt % of the biocompatible material biodegrades within six weeks of subcutaneous implantation in a Fisher 344 rat having an age between 9 and 11 weeks and a weight between 200 and 300 grams, as determined by testing on rats with a standard deviation of 25% (relative) of the biocompatible material weight and a population size of 10.

7. The scaffold of claim 1 wherein the composition is in the form of fibers having a diameter between 100 and 450 microns and a length:diameter aspect ratio of greater than 10:1 or bonded particles.

8. The scaffold of claim 1 wherein the biocompatible material does not convert to bone-precursor calcium phosphate compounds in phosphorus-containing mammalian fluids.

9. The scaffold of claim 1 wherein the Cu is in a concentration between 0.05 and 5 wt %.

10. The scaffold of claim 1 wherein the Cu is in a concentration between about 0.05 and about 5 wt %, wherein the composition is in the form of fibers, and wherein the scaffold has a trace element release rate of between about 1 and 25 E-7 moles of Cu, per gram of glass, per day.

11. The scaffold of claim 1 wherein the biocompatible material comprises:
    from 50 to about 80 wt % $B_2O_3$;
    one or more alkali oxides selected from the group consisting of $Li_2O$, $Na_2O$, $K_2O$, and $Rb_2O$;
    one or more alkaline earth oxides selected from the group consisting of MgO, SrO, BaO, and CaO; and
    Cu in a concentration between about 0.1 and about 2.5 wt %.

12. A method for facilitating vessel growth in repair, regeneration, and/or proliferation of bodily tissue in a mammal comprising implanting the scaffold of claim 1 into the mammal.

13. The scaffold of claim 1 wherein the compressive strength is at least 5 MPa.

14. The scaffold of claim 1 wherein the biocompatible material comprises self-bonded fibers or self-bonded particulates and the compressive strength is between 5 and 20 MPa.

15. The scaffold of claim 1 wherein the porosity is between about 15 and about 30 vol. %.

16. The scaffold of claim 1 wherein the porosity is between about 30 and 60 vol. %.

17. The scaffold of claim 1 wherein the porosity is between about 60 and 90 vol. %.

18. The scaffold of claim 1 wherein the biocompatible material comprises between 10 and 90 wt % of fibers of a first composition and between 10 and 90 wt % of fibers of a second composition different from the first composition.

19. The scaffold of claim 18 wherein the first composition comprises said Cu and said second composition does not comprise said Cu.

20. The scaffold of claim 1 wherein the biocompatible material comprises no more than 0.5 weight % Ca.

21. The scaffold of claim 20 wherein the biocompatible material comprises no more than 0.2 weight % Ca.

22. The scaffold of claim 20 wherein the composition comprises no more than 0.1 weight % Ca.

23. The scaffold of claim 1 wherein at least about 80 vol % of the pore volume of the scaffold is directly or indirectly through other pores accessible from the scaffold exterior, and therefore accessible to bodily fluids.

24. The scaffold of claim 2 wherein the scaffold body consists of said biocompatible material and said biocompatible material consists of said $B_2O_3$, said Cu, said one or more alkali oxides selected from the group consisting of $Li_2O$, $Na_2O$, $K_2O$, and $Rb_2O$, and said one or more alkaline earth oxides selected from the group consisting of MgO, SrO, BaO, and CaO.

* * * * *

UNITED STATES PATENT AND TRADEMARK OFFICE
CERTIFICATE OF CORRECTION

PATENT NO. : 8,287,896 B2  
APPLICATION NO. : 12/683280  
DATED : October 16, 2012  
INVENTOR(S) : Steven B. Jung et al.

Page 1 of 1

It is certified that error appears in the above-identified patent and that said Letters Patent is hereby corrected as shown below:

In the Specification

Column 1, line 7: "W81XWH-08-1-7065" should read -- W81XWH-08-1-0765 --.

Signed and Sealed this
Twenty-first Day of April, 2015

Michelle K. Lee
*Director of the United States Patent and Trademark Office*